(12) United States Patent
Ofek et al.

(10) Patent No.: US 11,129,573 B2
(45) Date of Patent: Sep. 28, 2021

(54) CATHETER ASSEMBLY INCLUDING MONITORING CAPABILITIES

(71) Applicant: C. R. Bard, Inc., Murray Hill, NJ (US)

(72) Inventors: Gidon Ofek, Honolulu, HI (US); Blake Allen, South Jordan, UT (US); Todd P. McFarland, Larue, TX (US); Samuel A. Francis, Salt Lake City, UT (US); Bret Hamatake, Grantsville, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 86 days.

(21) Appl. No.: 16/548,642

(22) Filed: Aug. 22, 2019

(65) Prior Publication Data
US 2019/0374162 A1    Dec. 12, 2019

Related U.S. Application Data

(62) Division of application No. 15/275,059, filed on Sep. 23, 2016, now Pat. No. 10,433,790.
(Continued)

(51) Int. Cl.
*A61B 5/00*          (2006.01)
*A61B 5/0205*      (2006.01)
(Continued)

(52) U.S. Cl.
CPC .......... *A61B 5/6852* (2013.01); *A61B 5/0022* (2013.01); *A61B 5/02055* (2013.01);
(Continued)

(58) Field of Classification Search
None
See application file for complete search history.

(56) References Cited

U.S. PATENT DOCUMENTS 3,739,943 A    6/1973   Wilhelmson et al.
3,809,871 A    5/1974   Howard et al.
(Continued)

FOREIGN PATENT DOCUMENTS

CA        2897940 A1    9/2014
EP         0331526 A1    9/1989
(Continued)

OTHER PUBLICATIONS

EP 16849804.6 filed Apr. 11, 2018 Supplementary European Search Report dated Dec. 11, 2018.
(Continued)

*Primary Examiner* — Brian T Gedeon
(74) *Attorney, Agent, or Firm* — Rutan & Tucker LLP

(57) ABSTRACT

A catheter assembly or other elongate tubular device for use in establishing vascular or other access within the body of a patient is disclosed. The catheter assembly is equipped with one or more sensors that enable monitoring of one or more physiological aspects of the patient or physical aspect of the catheter assembly itself when the catheter assembly is disposed within the patient. Such aspects include central venous pressure, body temperature, ECG heart signals, oxygen levels, ultrasound data, glucose, etc. The catheter assembly includes the ability to wirelessly transmit or otherwise forward data relating to the detected physiological parameters to another location, such as a patient electronic medical record, smartphone or other mobile device, nurse station, etc. Catheter assemblies configured to detect the frequency of catheter flushing, flushing quality, etc., are also disclosed.

21 Claims, 14 Drawing Sheets

Related U.S. Application Data

(60) Provisional application No. 62/233,184, filed on Sep. 25, 2015.

(51) Int. Cl.

| | | |
|---|---|---|
| *A61B 8/12* | (2006.01) | |
| *A61M 25/00* | (2006.01) | |
| *A61M 25/02* | (2006.01) | |
| *G16H 40/67* | (2018.01) | |
| *A61B 5/283* | (2021.01) | |
| *A61B 5/318* | (2021.01) | |
| *A61B 5/0215* | (2006.01) | |
| *A61B 5/024* | (2006.01) | |
| *A61B 5/08* | (2006.01) | |
| *A61B 5/145* | (2006.01) | |
| *A61M 39/28* | (2006.01) | |

(52) U.S. Cl.
CPC ............. *A61B 5/283* (2021.01); *A61B 5/318* (2021.01); *A61B 5/746* (2013.01); *A61B 8/12* (2013.01); *A61M 25/0097* (2013.01); *A61M 25/02* (2013.01); *G16H 40/67* (2018.01); *A61B 5/024* (2013.01); *A61B 5/02152* (2013.01); *A61B 5/0816* (2013.01); *A61B 5/14532* (2013.01); *A61B 5/14542* (2013.01); *A61B 5/412* (2013.01); *A61M 39/284* (2013.01); *A61M 2025/0002* (2013.01); *A61M 2230/04* (2013.01); *A61M 2230/50* (2013.01)

(56) References Cited

U.S. PATENT DOCUMENTS

| | | |
|---|---|---|
| 3,985,133 A | 10/1976 | Jenkins et al. |
| 4,078,562 A | 3/1978 | Friedman |
| 4,207,871 A | 6/1980 | Jenkins |
| 4,346,705 A | 8/1982 | Pekkarinen et al. |
| 4,370,983 A | 2/1983 | Lichtenstein |
| 4,373,527 A | 2/1983 | Fischell |
| 4,457,751 A | 7/1984 | Rodler |
| 4,474,309 A | 10/1984 | Solomon |
| 4,484,585 A | 11/1984 | Baier |
| 4,497,324 A | 2/1985 | Sullivan et al. |
| 4,507,974 A | 4/1985 | Yelderman |
| 4,530,696 A | 7/1985 | Bisera et al. |
| 4,533,346 A | 8/1985 | Cosgrove, Jr. et al. |
| 4,573,968 A | 3/1986 | Parker |
| 4,604,093 A | 8/1986 | Brown |
| 4,613,325 A | 9/1986 | Abrams |
| 4,670,007 A | 6/1987 | Wheeldon et al. |
| 4,747,828 A | 5/1988 | Tseo |
| 4,756,706 A | 7/1988 | Kerns et al. |
| 4,785,823 A | 11/1988 | Eggers et al. |
| 4,796,641 A | 1/1989 | Mills et al. |
| 4,809,710 A | 3/1989 | Williamson |
| 4,838,856 A | 6/1989 | Mulreany et al. |
| 4,846,191 A | 7/1989 | Brockway et al. |
| 4,979,940 A | 12/1990 | Bobo, Jr. et al. |
| 4,981,467 A | 1/1991 | Bobo, Jr. et al. |
| 5,000,190 A | 3/1991 | Petre |
| 5,000,664 A | 3/1991 | Lawless et al. |
| 5,024,668 A | 6/1991 | Peters et al. |
| 5,078,683 A | 1/1992 | Sancoff et al. |
| 5,108,364 A | 4/1992 | Takezawa et al. |
| 5,116,312 A | 5/1992 | Blankenship et al. |
| 5,171,301 A | 12/1992 | Vanderveen |
| 5,195,960 A | 3/1993 | Hossain et al. |
| 5,195,967 A | 3/1993 | Nakao et al. |
| 5,275,169 A | 1/1994 | Afromowitz et al. |
| 5,299,571 A | 4/1994 | Mastrototaro |
| 5,304,126 A | 4/1994 | Epstein et al. |
| 5,385,563 A | 1/1995 | Gross |
| 5,395,320 A | 3/1995 | Padda et al. |
| 5,431,627 A | 7/1995 | Pastrone et al. |
| 5,564,425 A | 10/1996 | Tonokura |
| 5,569,186 A | 10/1996 | Lord et al. |
| 5,676,145 A | 10/1997 | Bar-Lavie |
| 5,685,844 A | 11/1997 | Marttila |
| 5,758,643 A | 6/1998 | Wong et al. |
| 5,769,786 A | 6/1998 | Wiegel |
| 5,772,635 A | 6/1998 | Dastur et al. |
| 5,782,805 A | 7/1998 | Meinzer et al. |
| 5,840,068 A | 11/1998 | Cartledge |
| 5,916,153 A | 6/1999 | Rhea, Jr. |
| 5,935,105 A | 8/1999 | Manning et al. |
| 5,984,893 A | 11/1999 | Ward |
| 5,989,222 A | 11/1999 | Cole et al. |
| 6,006,123 A | 12/1999 | Nguyen et al. |
| 6,017,318 A | 1/2000 | Gauthier et al. |
| 6,033,366 A | 3/2000 | Brockway et al. |
| 6,213,972 B1 | 4/2001 | Butterfield et al. |
| 6,296,615 B1 | 10/2001 | Brockway et al. |
| 6,416,291 B1 | 7/2002 | Butterfield et al. |
| 6,659,959 B2 | 12/2003 | Brockway et al. |
| 6,685,668 B1 | 2/2004 | Cho et al. |
| 6,712,771 B2 | 3/2004 | Haddock et al. |
| 6,757,630 B2 | 6/2004 | McClendon et al. |
| 6,770,055 B2 | 8/2004 | Bierman et al. |
| 6,932,114 B2 | 8/2005 | Sparks |
| 6,986,746 B2 | 1/2006 | Fox et al. |
| 6,999,809 B2 | 2/2006 | Currier et al. |
| 7,090,645 B2 | 8/2006 | Fox et al. |
| 7,108,680 B2 | 9/2006 | Rohr et al. |
| 7,138,088 B2 | 11/2006 | Wariar et al. |
| 7,150,735 B2 | 12/2006 | Hickle |
| 7,220,240 B2 | 5/2007 | Struys et al. |
| 7,338,464 B2 | 3/2008 | Blischak et al. |
| 7,471,994 B2 | 12/2008 | Ford et al. |
| 7,473,244 B2 | 1/2009 | Frazier et al. |
| 7,515,954 B2 | 4/2009 | Harlev et al. |
| 7,608,042 B2 | 10/2009 | Goldberger et al. |
| 7,645,258 B2 | 1/2010 | White et al. |
| 7,654,976 B2 | 2/2010 | Peterson et al. |
| 7,654,982 B2 | 2/2010 | Carlisle et al. |
| 7,695,448 B2 | 4/2010 | Cassidy et al. |
| 7,713,241 B2 | 5/2010 | Cartledge et al. |
| 7,729,752 B2 | 6/2010 | Harlev et al. |
| 7,819,817 B2 | 10/2010 | Rahn |
| 7,918,805 B2 | 4/2011 | Chelak |
| 7,927,313 B2 | 4/2011 | Stewart et al. |
| 7,930,018 B2 | 4/2011 | Harlev et al. |
| 7,937,136 B2 | 5/2011 | Harlev et al. |
| 7,953,475 B2 | 5/2011 | Harlev et al. |
| 7,957,791 B2 | 6/2011 | Harlev et al. |
| 7,957,792 B2 | 6/2011 | Harlev et al. |
| 8,016,766 B2 | 9/2011 | Goedje et al. |
| 8,034,050 B2 | 10/2011 | Sharareh et al. |
| 8,082,018 B2 | 12/2011 | Duchon et al. |
| 8,092,385 B2 | 1/2012 | Goldberger et al. |
| 8,105,269 B2 | 1/2012 | Zhou |
| 8,105,282 B2 | 1/2012 | Susi et al. |
| 8,163,237 B2 | 4/2012 | Crawford et al. |
| 8,182,445 B2 | 5/2012 | Moubayed et al. |
| 8,200,308 B2 | 6/2012 | Zhang et al. |
| 8,219,413 B2 | 7/2012 | Martinez et al. |
| 8,233,957 B2 | 7/2012 | Merz et al. |
| 8,264,363 B2 | 9/2012 | DelCastilio et al. |
| 8,267,887 B2 | 9/2012 | Mohl |
| 8,287,488 B2 | 10/2012 | Wiegel |
| 8,348,844 B2 | 1/2013 | Kunjan et al. |
| 8,388,582 B2 | 3/2013 | Eubanks et al. |
| 8,425,417 B2 | 4/2013 | Leach et al. |
| 8,433,394 B2 | 4/2013 | Harlev et al. |
| 8,475,448 B2 | 7/2013 | Sharareh et al. |
| 8,500,685 B2 | 8/2013 | Mohl |
| 8,565,857 B2 | 10/2013 | Lips et al. |
| 8,612,257 B2 | 12/2013 | Zaitsu et al. |
| 8,613,753 B2 | 12/2013 | Angel et al. |
| 8,622,989 B2 | 1/2014 | Martin |
| 8,668,712 B2 | 3/2014 | Angel |
| 8,672,875 B2 | 3/2014 | Vanderveen et al. |
| 8,777,977 B2 | 7/2014 | Angel |

(56) References Cited

U.S. PATENT DOCUMENTS

| | | |
|---|---|---|
| 8,794,830 B2 | 8/2014 | Fang et al. |
| 8,795,203 B2 | 8/2014 | Williams et al. |
| 8,849,382 B2 | 9/2014 | Cox et al. |
| 8,858,185 B2 | 10/2014 | Johnson et al. |
| 8,911,367 B2 | 12/2014 | Brister et al. |
| 8,936,755 B2 | 1/2015 | Gable et al. |
| 8,961,461 B2 | 2/2015 | Stewart et al. |
| 8,974,394 B2 | 3/2015 | Frinak et al. |
| 9,095,653 B2 | 8/2015 | Willmann et al. |
| 9,135,393 B1 | 9/2015 | Blomquist |
| 9,138,533 B2 | 9/2015 | Thompson et al. |
| 9,227,025 B2 | 1/2016 | Butterfield et al. |
| 9,272,086 B2 | 3/2016 | Williams et al. |
| 9,327,072 B2 | 5/2016 | Zhang et al. |
| 9,352,078 B2 | 5/2016 | Roger et al. |
| 9,375,531 B2 | 6/2016 | Lee et al. |
| 9,378,334 B2 | 6/2016 | Lee et al. |
| 9,414,782 B2 | 8/2016 | Braig et al. |
| 9,446,191 B2 | 9/2016 | Zhang et al. |
| 9,468,718 B2 | 10/2016 | Hung et al. |
| 9,501,619 B2 | 11/2016 | Portnoy et al. |
| 9,526,825 B2 | 12/2016 | McTaggart et al. |
| 9,586,001 B2 | 3/2017 | Halbert et al. |
| 9,592,029 B2 | 3/2017 | Buckberry |
| 9,814,866 B1 | 11/2017 | Goswami |
| 10,433,790 B2 | 10/2019 | Ofek et al. |
| 2002/0156417 A1 | 10/2002 | Rich et al. |
| 2003/0106553 A1 | 6/2003 | Vanderveen |
| 2003/0195428 A1 | 10/2003 | Brockway et al. |
| 2004/0051368 A1 | 3/2004 | Caputo et al. |
| 2004/0167385 A1 | 8/2004 | Rioux et al. |
| 2005/0197585 A1 | 9/2005 | Brockway et al. |
| 2006/0015074 A1* | 1/2006 | Lynn .................. A61M 39/225 604/250 |
| 2006/0135940 A1 | 6/2006 | Joshi |
| 2006/0229531 A1 | 10/2006 | Goldberger et al. |
| 2008/0146940 A1 | 6/2008 | Jenkins et al. |
| 2008/0194988 A1 | 8/2008 | Nakamura et al. |
| 2009/0006267 A1 | 1/2009 | Fergusson et al. |
| 2009/0054754 A1 | 2/2009 | McMahon et al. |
| 2009/0177090 A1 | 7/2009 | Grunwald et al. |
| 2009/0221956 A1 | 9/2009 | Abrams et al. |
| 2009/0234328 A1* | 9/2009 | Cox .................... A61B 8/0841 604/523 |
| 2010/0041973 A1 | 2/2010 | Vu et al. |
| 2010/0222664 A1 | 9/2010 | Lemon et al. |
| 2011/0004198 A1 | 1/2011 | Hoch |
| 2011/0046457 A1* | 2/2011 | Gottlieb ................ A61B 5/415 600/309 |
| 2011/0092955 A1 | 4/2011 | Purdy et al. |
| 2011/0105877 A1 | 5/2011 | Wilt et al. |
| 2011/0144540 A1 | 6/2011 | Shen et al. |
| 2011/0184266 A1 | 7/2011 | Levin |
| 2011/0257593 A1 | 10/2011 | Kalpin et al. |
| 2011/0264044 A1 | 10/2011 | Bartz et al. |
| 2011/0313394 A1 | 12/2011 | Bobo, Sr. |
| 2011/0319728 A1 | 12/2011 | Petisce et al. |
| 2013/0030262 A1 | 1/2013 | Burnett et al. |
| 2013/0066166 A1 | 3/2013 | Burnett et al. |
| 2014/0180330 A1 | 6/2014 | Angel et al. |
| 2014/0243688 A1 | 8/2014 | Caron et al. |
| 2014/0276198 A1 | 9/2014 | Dunung et al. |
| 2015/0335820 A1 | 11/2015 | De Armond et al. |
| 2016/0287780 A1 | 10/2016 | Lee et al. |
| 2016/0287784 A1 | 10/2016 | Straw et al. |
| 2016/0346462 A1 | 12/2016 | Adams et al. |
| 2017/0086746 A1 | 3/2017 | Ofek et al. |
| 2017/0136177 A1 | 5/2017 | Lee et al. |
| 2017/0143898 A1 | 5/2017 | Grosse-Wentrup et al. |
| 2018/0256038 A1 | 9/2018 | Shah |

FOREIGN PATENT DOCUMENTS

| | | |
|---|---|---|
| WO | 1989011244 A1 | 11/1989 |
| WO | 1993013709 A1 | 7/1993 |
| WO | 01/074263 A1 | 10/2001 |
| WO | 01/095787 A2 | 12/2001 |
| WO | 02/43789 A2 | 6/2002 |
| WO | 03/11125 A1 | 2/2003 |
| WO | 03/77751 A1 | 9/2003 |
| WO | 03/94715 A1 | 11/2003 |
| WO | 2004007012 A2 | 1/2004 |
| WO | 2004087010 A2 | 10/2004 |
| WO | 2006015230 A2 | 2/2006 |
| WO | 2006055654 A1 | 5/2006 |
| WO | 2006055658 A1 | 5/2006 |
| WO | 2007146864 A2 | 12/2007 |
| WO | 2008032249 A2 | 3/2008 |
| WO | 2010011846 A1 | 1/2010 |
| WO | 2010/022370 A1 | 2/2010 |
| WO | 2010054312 A1 | 5/2010 |
| WO | 2011/094631 A1 | 8/2011 |
| WO | 2012122267 A1 | 9/2012 |
| WO | 2013061280 A1 | 5/2013 |
| WO | 2014/151068 A2 | 9/2014 |
| WO | 2015/074032 A1 | 5/2015 |
| WO | 2017/053882 A1 | 3/2017 |
| WO | 2019/228991 A1 | 12/2019 |

OTHER PUBLICATIONS

Nova Biomedical: World Leader in Biosensor Technology—Hospital Connectivity Glucose/Ketone Monitoring System. http://www.novabio.uk/statstrip-ketone/. Last accessed Sep. 19, 2016.

PCT/US2016/053566 filed Sep. 23, 2016 International Search Report and Written Opinion dated Dec. 15, 2016.

U.S. Appl. No. 15/275,059, filed Sep. 23, 2016 Final Office Action dated Feb. 1, 2019.

U.S. Appl. No. 15/275,059, filed Sep. 23, 2016 Non-Final Office Action dated Aug. 6, 2018.

U.S. Appl. No. 15/275,059, filed Sep. 23, 2016 Restriction Requirement dated Jun. 11, 2018.

Forrester, et al., "Thermodilution Cardiac Output Determination With a single Flow—Directed Catheter", American Heart Journal, vol. 83, No. 3, 1972.

Normann et al., "A Continuous Cardiac Output Computer Based on Thermodilution Principles", Annals of Biomedical Engineering, vol. 17, 1989.

Taylor, et al., "Understanding Techniques for Measuring Cardiac Output", Biomedical Instrumentation & Technology, May/Jun. 1990.

Temperature monitoring in catheters: "The Bard/BD Standard 400 Series Temperature-Sensing Foley Catheters" ( 2018).

PCT/US2021/012529 filed Jan. 7, 2021 International Search Report and Written Opinion dated Mar. 26, 2021.

* cited by examiner

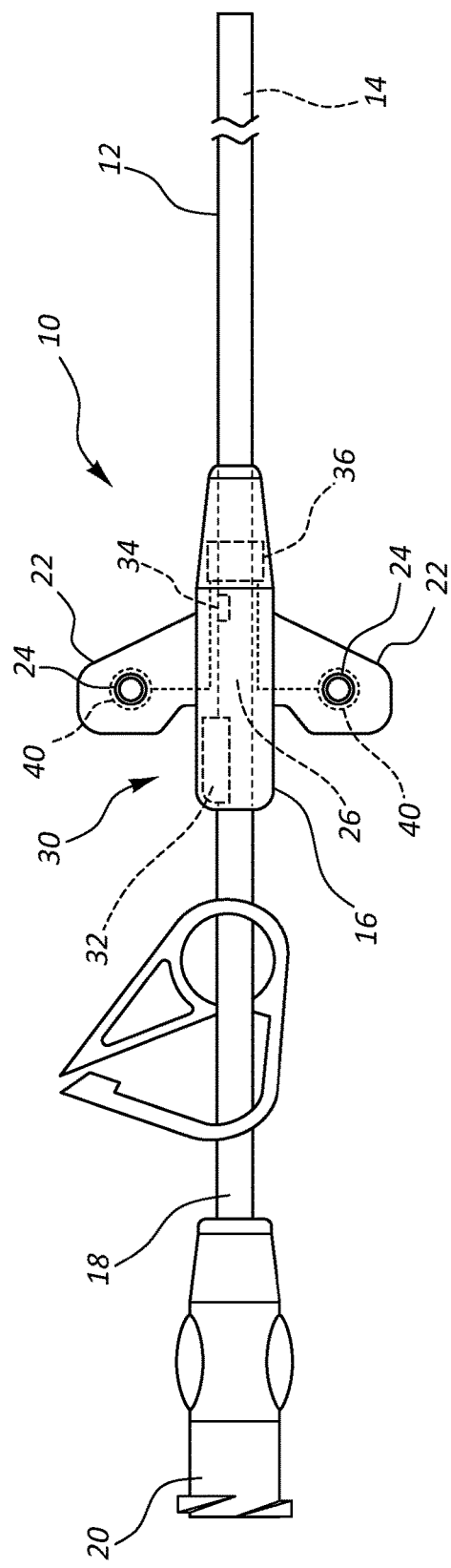
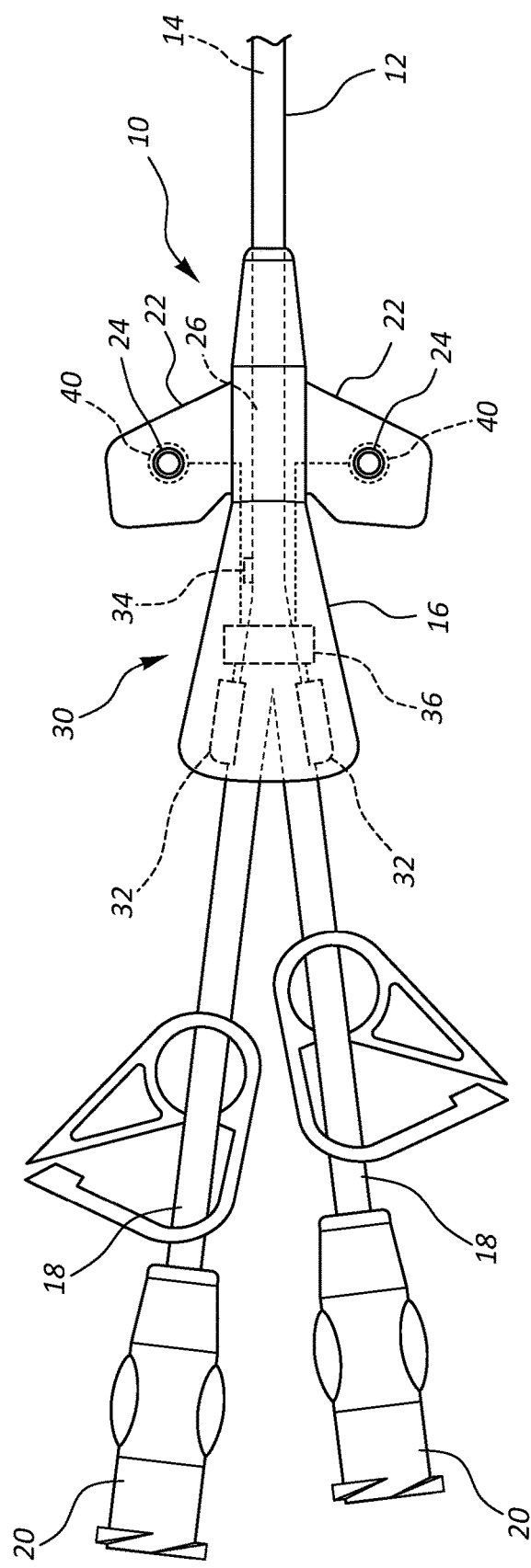
FIG. 1
FIG. 2

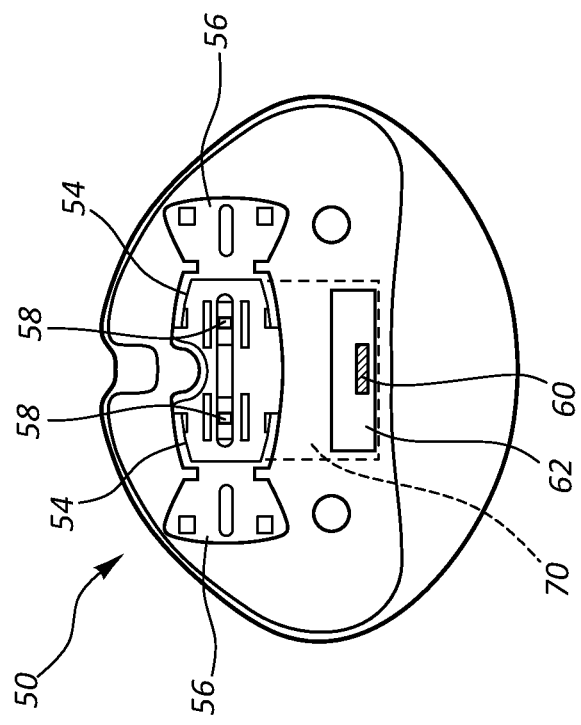
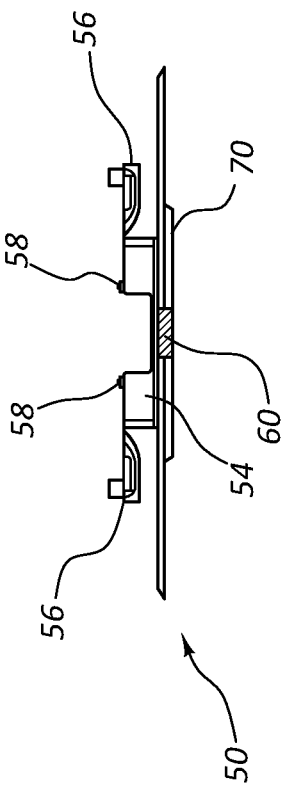
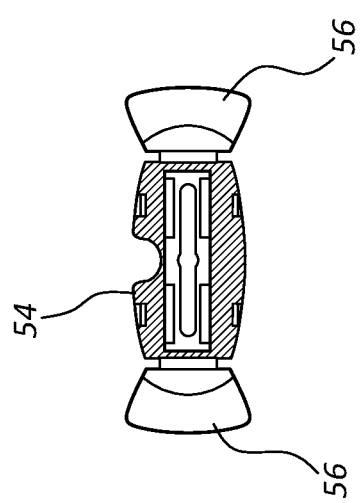
FIG. 5A
FIG. 5C
FIG. 5B

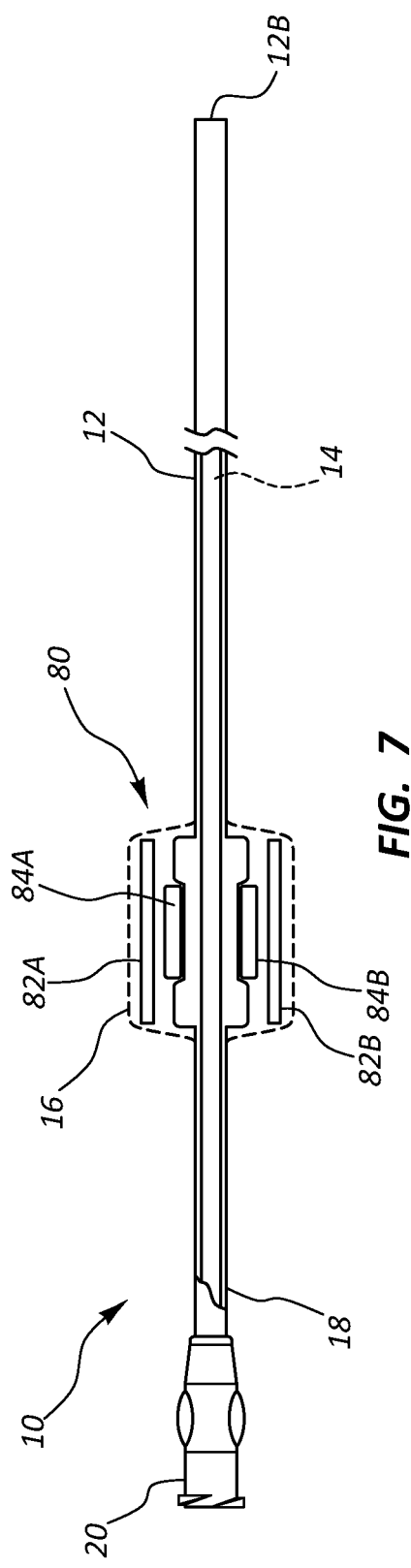
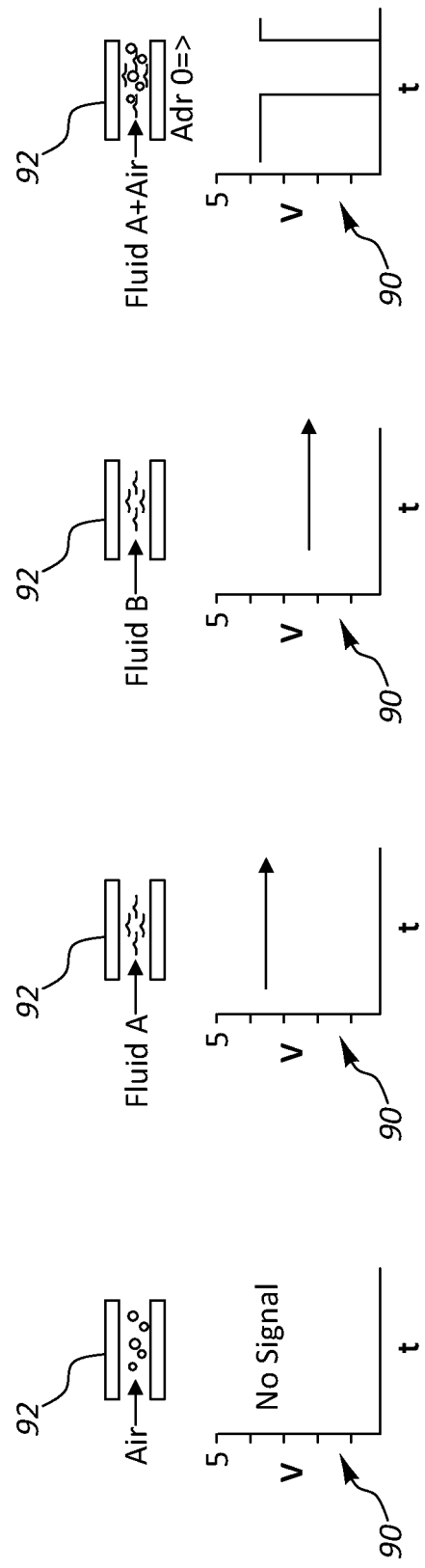
FIG. 7
FIG. 8A  FIG. 8B  FIG. 8C  FIG. 8D

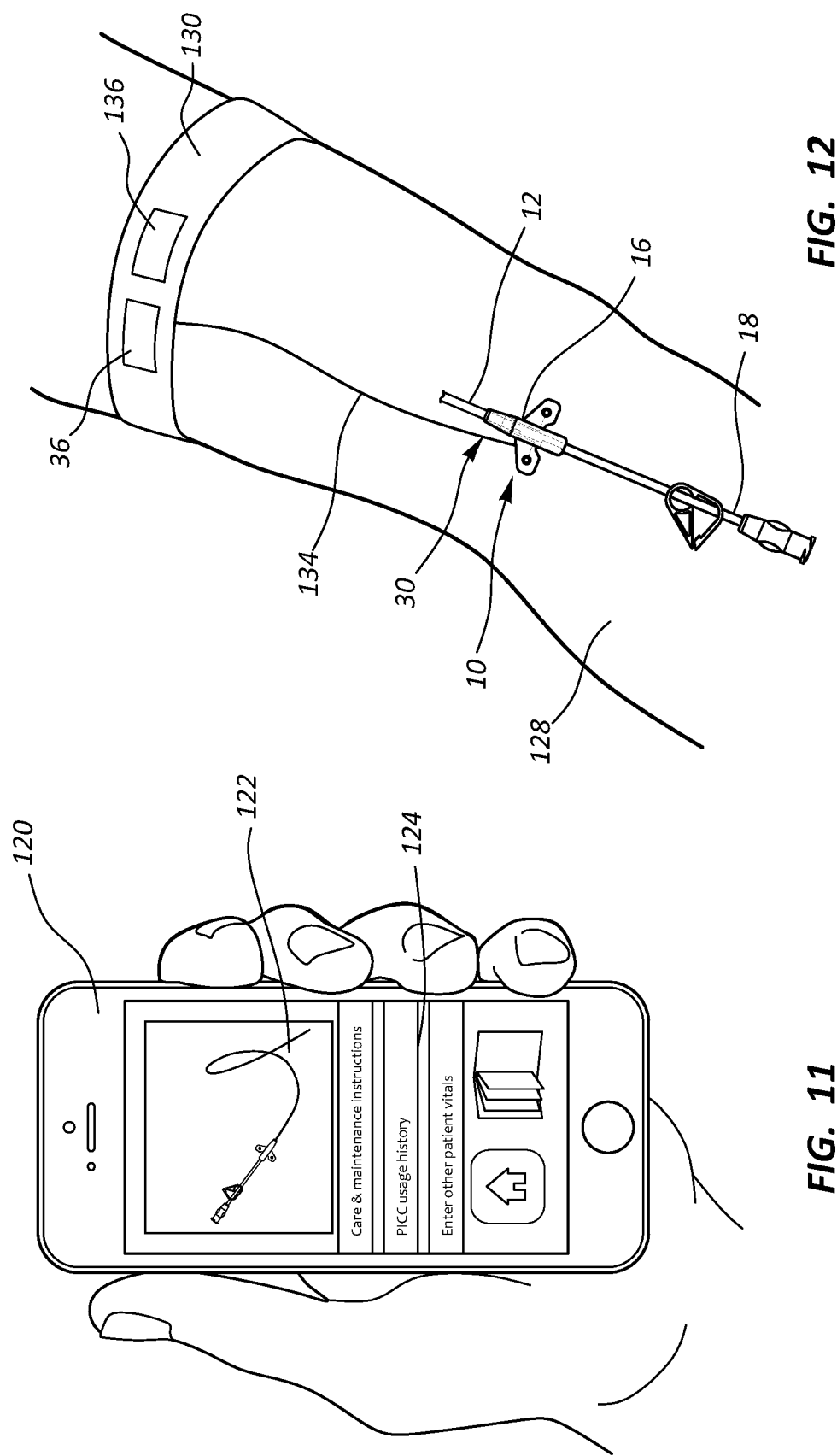

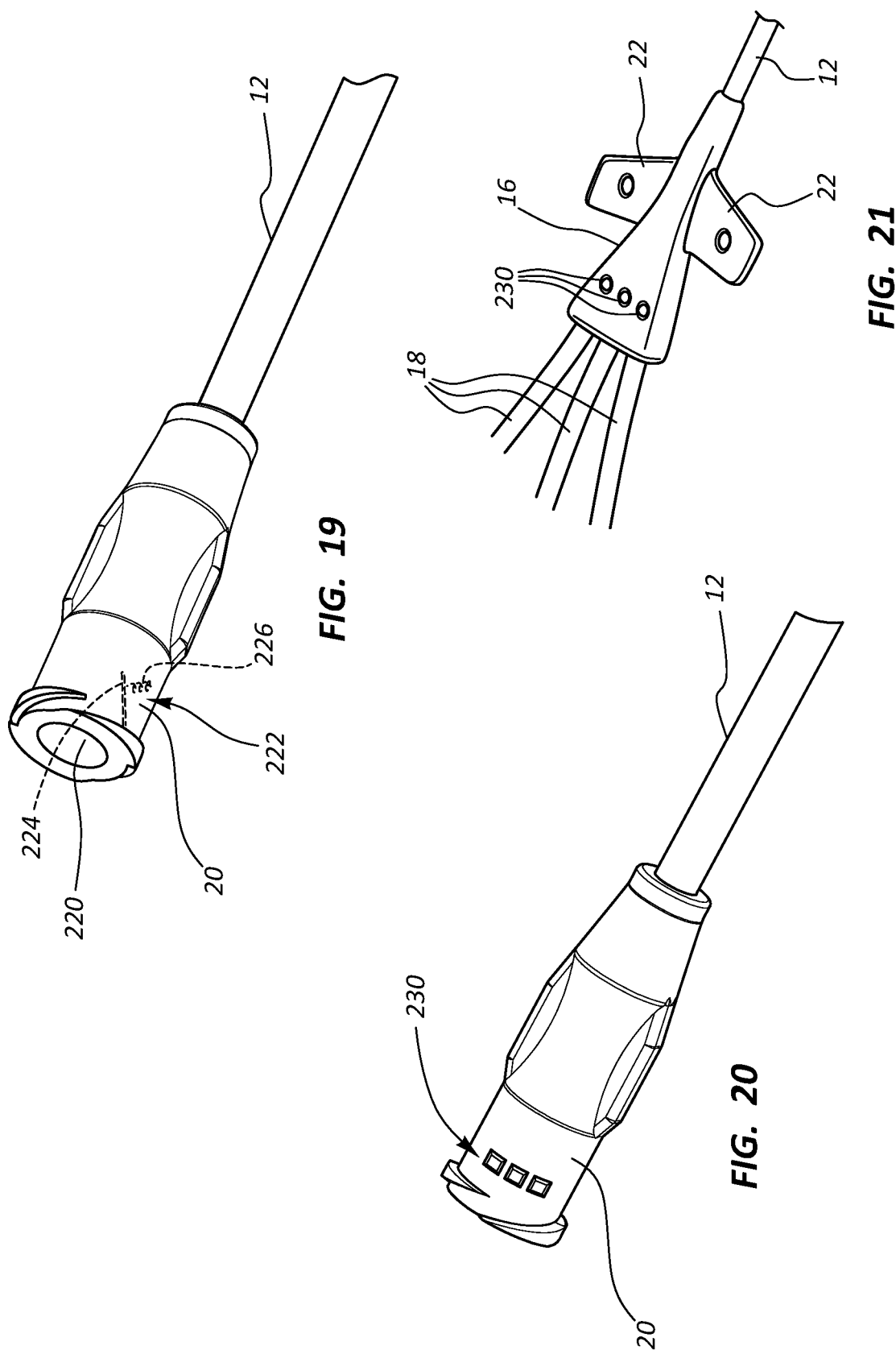

CATHETER ASSEMBLY INCLUDING MONITORING CAPABILITIES

CROSS-REFERENCE TO RELATED APPLICATIONS

This application is a division of U.S. patent application Ser. No. 15/275,059, filed Sep. 23, 2016, now U.S. Pat. No. 10,433,790, which claims the benefit of U.S. Provisional Patent Application No. 62/233,184, filed Sep. 25, 2015, and titled "Catheter Assembly Including Monitoring Capabilities," which is incorporated herein by reference in its entirety.

BRIEF SUMMARY

Briefly summarized, embodiments of the present invention are directed to a catheter assembly or other elongate tubular device for use in establishing vascular or other access within the body of a patient. The catheter assembly is equipped with one or more sensors that enable monitoring of one or more physiological aspect or other parameter of the patient, and/or physical aspects of the catheter assembly itself or its operation, when the catheter assembly is disposed within the patient. Such parameters include central venous pressure, body temperature, ECG heart signals, oxygen levels, ultrasound data, glucose, etc. The catheter assembly includes the ability to wirelessly transmit or otherwise forward data relating to the detected physiological/physical aspects to another location, such as a patient electronic medical record, smartphone or other mobile device, nurse station, etc. Catheter assemblies configured to detect the frequency of catheter flushing, flushing quality, etc., are also disclosed.

In one embodiment, therefore, a catheter assembly for insertion into a body of a patient is disclosed and comprises an elongate catheter tube defining at least one lumen extending between a proximal end and a distal end, a bifurcation hub operably attached to the catheter tube, and an extension leg operably attached to the bifurcation hub, the bifurcation hub and extension leg defining at least one fluid passageway in fluid communication with the at least one lumen of the catheter tube. At least one sensor is included with the catheter assembly, the at least one sensor being configured to detect a physiological aspect of the patient and/or physical aspect of the catheter assembly. A communication module is also included and is configured to wirelessly transmit data sensed by the at least one sensor to a receipt location.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 1 is a plan view of a catheter assembly in accordance with one embodiment;

FIG. 2 is a plan view of a catheter assembly in accordance with one embodiment;

FIGS. 5A-5C are various views of a catheter securement device according to one embodiment;

FIG. 7 is a partial cross-sectional view of a catheter assembly in accordance with one embodiment;

FIGS. 8A-8D are various views of an ultrasound signal graph;

FIG. 11 is a view of a smartphone in accordance with one embodiment;

FIG. 12 is a perspective view of a catheter assembly and an auxiliary device in accordance with one embodiment;

FIG. 19 is a perspective view of a luer connector according to one embodiment;

FIG. 20 is a perspective view of a luer connector of a catheter assembly according to one embodiment;

FIG. 21 is a perspective view of a bifurcation hub of a catheter assembly according to one embodiment;

DETAILED DESCRIPTION OF SELECTED EMBODIMENTS

Figure 3:
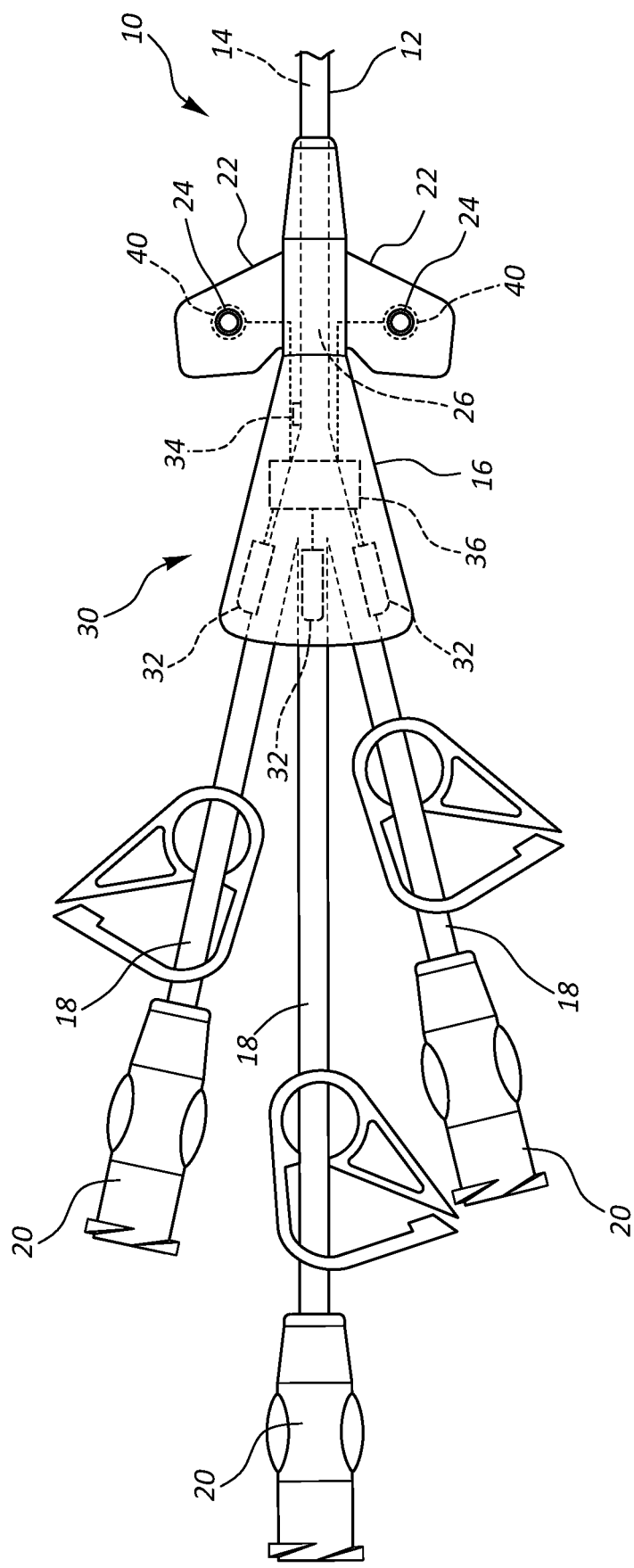
FIG. 3 is a plan view of a catheter assembly in accordance with one embodiment.

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present disclosure are generally directed to a catheter assembly or other elongate tubular device for use in establishing vascular or other access within the body of a patient, together with associated components.

Examples of such catheters include PICCs, central venous catheters, arterial catheters, Foley-type and urinary catheters, peripheral IVs, midline catheters, intermediate-dwell catheters, feeding tubes, etc.

The catheter assembly or associated component is equipped with one or more sensors that enable monitoring of one or more physiological aspect or other parameters of the patient, and/or physical aspects of the catheter assembly itself or its operation, when the catheter assembly is disposed within the patient. Such aspects include central venous pressure, body temperature, ECG heart signals, oxygen levels, ultrasound data, etc. The sensor(s) included with the catheter assembly are placed so as to enable detection of data related to these and/or other parameters. In one embodiment, the one or more sensors are disposed in or proximate to a hub of the catheter assembly, though a variety of other locations are also possible. Moreover, other components and structures associated with the catheter assembly, such as a needleless connector for instance, can include one or more sensors for monitoring physiological/physical aspects.

Further, the catheter assembly includes the ability to wirelessly transmit or otherwise forward data relating to the detected physiological aspects/physical aspect to another location, also referred to herein as a receipt location. Examples of data receipt locations include an patient electronic medical record ("EMR"), a patient monitoring apparatus, a smartphone or other mobile device, a tablet, a storage location, a computer server, a nurse station, or a variety of other destinations.

Reference is first made to FIG. 1, which depicts various details of a catheter assembly ("catheter"), generally designated at 10, in accordance with one embodiment. As shown, the catheter 10 includes an elongate catheter tube 12 defining one or more lumens 14 extending between a proximal end 12A and a distal end 12B thereof. The proximal end 12A of the catheter tube is operably connected to a bifurcation hub ("hub") 16, which in turn is operably connected to one or more extension legs 18. A connector 20, such as a Luer connector, is disposed on a proximal end of the extension leg 18. The hub 16 includes two suture wings 22 that oppositely extend from the body of the hub 16. Each suture wing 22 includes a suture hole 24. Note that the hub 16 is also referred to herein as a "bifurcation hub" even in cases where only one fluid passageway is defined therethrough.

In accordance with one embodiment, one or more sensors, also referred to herein as a "sensor array" 30, are included with the catheter 10 to enable the detection of date relating to one or more physiological aspects of the patient and/or physical aspects of the catheter when the catheter tube 12 is disposed in the vasculature (as discussed here) or other suitable internal portion of the body of the patient. In the present embodiment, multiple sensors are included with the catheter 10, though the number, type, size, placement, function, and desired uses of the various sensors can vary from what is shown and described herein. Note that the sensor array 30 can, in one embodiment, include only one sensor. Note also that, where only one of a particular sensor is discussed below, it is appreciated that more than one of a particular type of sensor can be included, in the same or different locations within the catheter assembly.

As shown in FIG. 1, a pressure sensor 32 is included as part of the sensor array 30. In the present embodiment, the pressure sensor 32 includes a central venous pressure ("CVP") sensor and is disposed so as enable venous pressure of the patient to be sensed via the fluid (such as blood and/or saline) typically present within the lumen 14 of the catheter tube 12. As shown, in the present embodiment the pressure sensor 32 is disposed within the hub 16 so as to be in operable communication with a fluid passageway 26 within the hub that is in turn in fluid communication with the lumen 14 of the single-lumen catheter tube 12 shown in FIG. 1. Other pressure sensor locations can also employed, including within the catheter tube 12, the extension leg 18, etc. In one embodiment, the pressure sensor 32 is a medical pressure sensor NPC-100 or NPC-120, manufactured by Amphenol Corporation, though other pressure sensors may also be employed. In another embodiment, the pressure sensor includes a strain-sensitive Wheatstone bridge. The sensing surface of the pressure sensor 32 in the present embodiment is in direct contact with fluid present in the fluid passageway of the hub 16. Note that the size, shape, and other configuration of the hub 16 may be increased from what is shown and described herein in order to accommodate the sensor array 30, in one embodiment.

An ECG sensor 34, also referred to herein as an ECG electrode or electrical sensor, is also included with the catheter assembly to enable ECG signals emanating from the heart of the patient to be detected, in conjunction with an additional ECG sensor/electrode located on the patient's skin or external portion of the catheter assembly/proximate the catheter assembly, in one embodiment. As shown, in the present embodiment the ECG sensor 34 is also disposed within the hub 16 so as to be in direct contact with fluid present in the hub fluid passageway 26 and the lumen 14 of the catheter tube 12. Other ECG sensor locations can also be employed, including within the catheter tube 12, the extension leg 18, etc. In the present embodiment, the ECG sensor 34 includes a conductive wire that is able to detect ECG signals of the patient heart that are present in the fluid of the hub fluid passageway 26 and catheter tube lumen 14, though other types of ECG sensors can be employed. Further details regarding a system and method for using an ECG sensor for guiding the catheter assembly to a desired position within the body of a patient can be found in U.S. Pat. No. 8,849,382, entitled "Apparatus and Display Methods Relating to Intravascular Placement of a Catheter," which is incorporated herein by reference in its entirety.

As described, the sensor array 30—including here the pressure sensor 30 and the ECG sensor 34—is disposed within the hub 16, which is sized to provide the needed volume for such sensors. Note that the size, shape, and configuration of the hub 16 can vary from what is shown and described in order to house the sensor(s). In other embodiments, the sensors can be located in other portions of the catheter 10, including along or at either end of the catheter tube 12, the extension leg(s) 18, etc. Also note that a variety of sensors for detecting body measurements, physiological aspects of the patient, and/or physical aspects of the catheter can be included with the catheter assembly, some of which are discussed further below.

FIG. 1 further shows that the hub 16 (or other suitable location) includes a printed circuit board ("PCB") 36 that is configured to govern operation of the sensor array 30, here including the pressure sensor 30 and the ECG sensor 34. In one embodiment, the PCB 36 includes a microprocessor for governing sensor operation. In one embodiment, the PCB 36 can further include a power source for powering the sensor array 30, though in other embodiments the power source can be remotely disposed from the PCB, and even the catheter 10. A non-volatile memory storage location, such as flash memory for instance, can also be included on the PCB 36 to enable data sensed by the sensors of the sensor array 30 to be temporarily or permanently stored thereon. The storage location can be accessible by a user or can be transmitted to a desired location in a manner described below.

In the present embodiment, the PCB 36 further includes a transmission module, such as a radio for enabling the PCB to transmit sensor data wirelessly to another receipt location, such as those referred to further above. Such wireless transmission can occur via Bluetooth, Wi-Fi, radiofrequency, near-field communication ("NFC"), GPS, ANT, ZigBee, or other manner utilizing electromagnetic radiation. In another embodiment, the sensor data can be transmitted from the catheter 10 via a physical connection, such as via a removable physical connection, wires, etc. In another embodiment and as mentioned, sensor data, e.g., central venous pressure, ECG signals, temperature, etc., are stored in a memory location included on the PCB 36, or other location on the catheter 10. In yet another embodiment, the PCB 36 includes a clock/timer circuit.

Figure 4A:
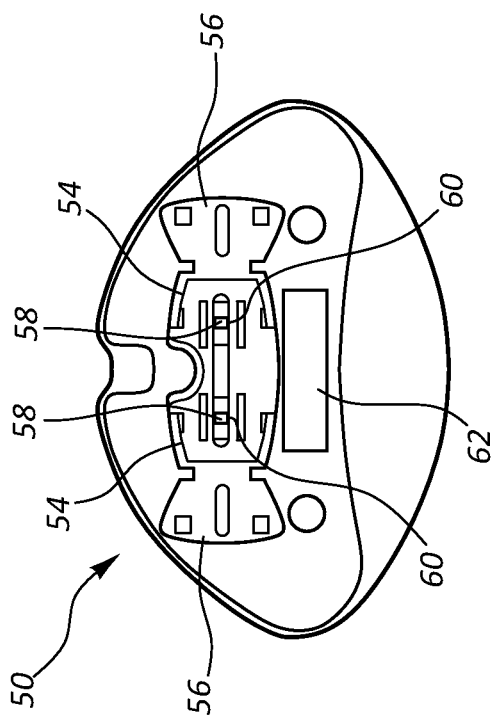
FIGS. 4A-4C are various views of a catheter securement device according to one embodiment.
Figure 4C:
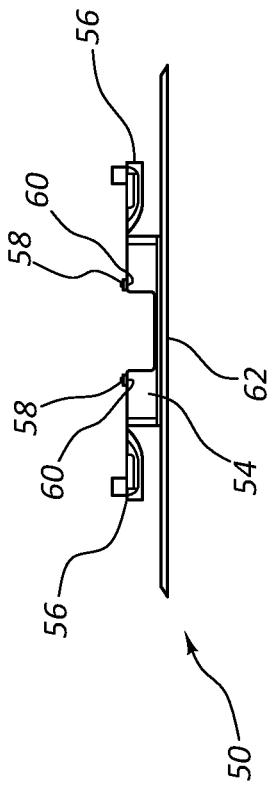
Figure 4B:
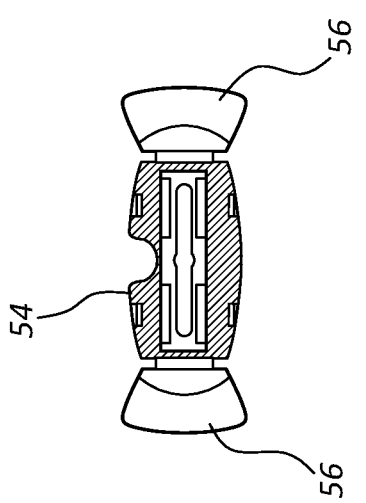

In the present embodiment of FIG. 1, the suture holes 24 of the suture wings 22 are configured to include electrical contacts to provide power to the sensors 30 and 34 of the sensor array 30, as well as to the PCB 36. In particular, an annular electrical contact 40 is included in each suture hole 24 of the bifurcation hub suture wings 22, with the electrical contacts being operably connected to the PCB 36 and sensor array 30. A securement device, such as the securement device 50 shown in FIGS. 4A-4C, is configured to be placed on the skin of the patient and operably connect with and secure in place the catheter 10 once the distal portion of the catheter has been inserted into the patient. To that end, the securement device 50 includes a retainer 54 mounted to an adhesive pad, and securement arms that are hinged so as to removably pivot atop the suture wings 22 of the bifurcation hub 16 (in a snap-fit arrangement) to secure the bifurcation hub in place.

In the present embodiment, the securement device 50 includes additional functionality to provide power to the sensor array 30 and PCB 36. In detail, the securement device 50 includes two posts 58, each of which is configured to serve as an electrical contact 60 and each of which is operably connected with a battery 62, also included in the securement device. The posts 58 are configured to be received within the corresponding suture holes 24 of the catheter suture wings 22 such that electrical contact is established with the electrical contacts 40 of the suture holes. The battery 62 included on the securement device 50 can, in this way, provide electrical power to the sensors 32, 34 and the PCB 36 of the catheter hub 16. Of course, other external power sources can be employed. In one embodiment, electrical contacts between the catheter and the securement device can also be utilized to transfer sensor data therebetween. In another embodiment, the securement device can include a radio or other mode for transmitting sensor data received from the catheter. In yet another embodiment, the PCB or a sensor can be included on the securement device. It is appreciated that the size, shape, and other configuration of the securement device can vary from what is shown and described herein.

FIGS. 5A-5C depict details of the securement device 50 according to another embodiment, wherein the securement device includes a pod 70 that includes a PCB and a battery for use with the sensor array 30 included on the catheter 10, for instance. This eliminates the need for the PCB and/or battery to be disposed on the catheter 10 itself. FIGS. 5A and 5C show that the pod 70 includes the electrical contact 60 on an upper surface of the retainer 54, where it is configured to electrically connect with a corresponding electrical contact on the hub 16 of the catheter 10. Thus, when the hub 16 is removably retained by the securement arms 56 of the securement device 50, the sensor array 30 is powered and governed by the battery and PCB of the pod 70. In one embodiment, the pod 70 is configured to be removable from the securement device 50, thus enabling it to be reusable with successive securement devices. This may be helpful when the catheter 10 and/or the securement device 50 are changed out. Thus, the pod 70—including the PCB, battery, and/or one or more sensors, etc. —can be removed from the securement device and placed in another, thus saving resources and cost. Note also that battery and PCB can be disposed in other locations as well. These and other variations are therefore contemplated. Further details regarding a catheter securement device related to those described herein can be found in U.S. Pat. No. 6,770,055, entitled "Universal Catheter Anchoring System," which is incorporated herein by reference in its entirety.

Additionally, in one embodiment the securement device 50 can include an ECG sensor (e.g., an electrode) that can cooperate with the ECG sensor 34 of the catheter 10, thus enabling dual ECG signals to be detected and used to determine proximity of the distal end 12B of the catheter tube 12 with respect to the heart. This configuration can also be used to determine malposition of the catheter tube distal end 12B, both during initial catheter placement and subsequently during the indwelling of the catheter within the patient. Sensor data from the pressure sensor 30 can also be used in connection with the ECG signals to further detect catheter tube distal end malpositions, in one embodiment.

FIGS. 2 and 3 show dual and triple-lumen catheter configurations, respectively, in contrast to the single-lumen configuration of FIG. 1. As with that of FIG. 1, the catheters 10 shown in FIGS. 2 and 3 each include sensor arrays 30 similar to that shown in FIG. 1, including corresponding pressure sensors 32, ECG sensors 34, and PCBs 36. The electrical contacts 40 for electrical connection with electrical contacts 60 of the securement device 50 (FIGS. 4A-4C) are also shown. Note that each extension leg 18 of the catheters 10 in FIGS. 2 and 3 includes a corresponding one of the pressure sensors 32 such that pressure data may be sensed in each extension leg. In other embodiments, more or fewer sensors than what is shown here can be employed for sensing physiological aspects of the patient and/or physical aspects of the catheter assembly including, for instance, lactic acid sensors, oxygen sensors, ultrasound componentry, GPS location sensors, temperature sensors, sizing sensors to measure intraluminal diameter, fluid velocity sensors, glucose meters, oxygen sensors, lactic acid sensors, cardiac output sensors, accelerometers, blood volumetric and cardiac output sensors, etc.

Figure 6:
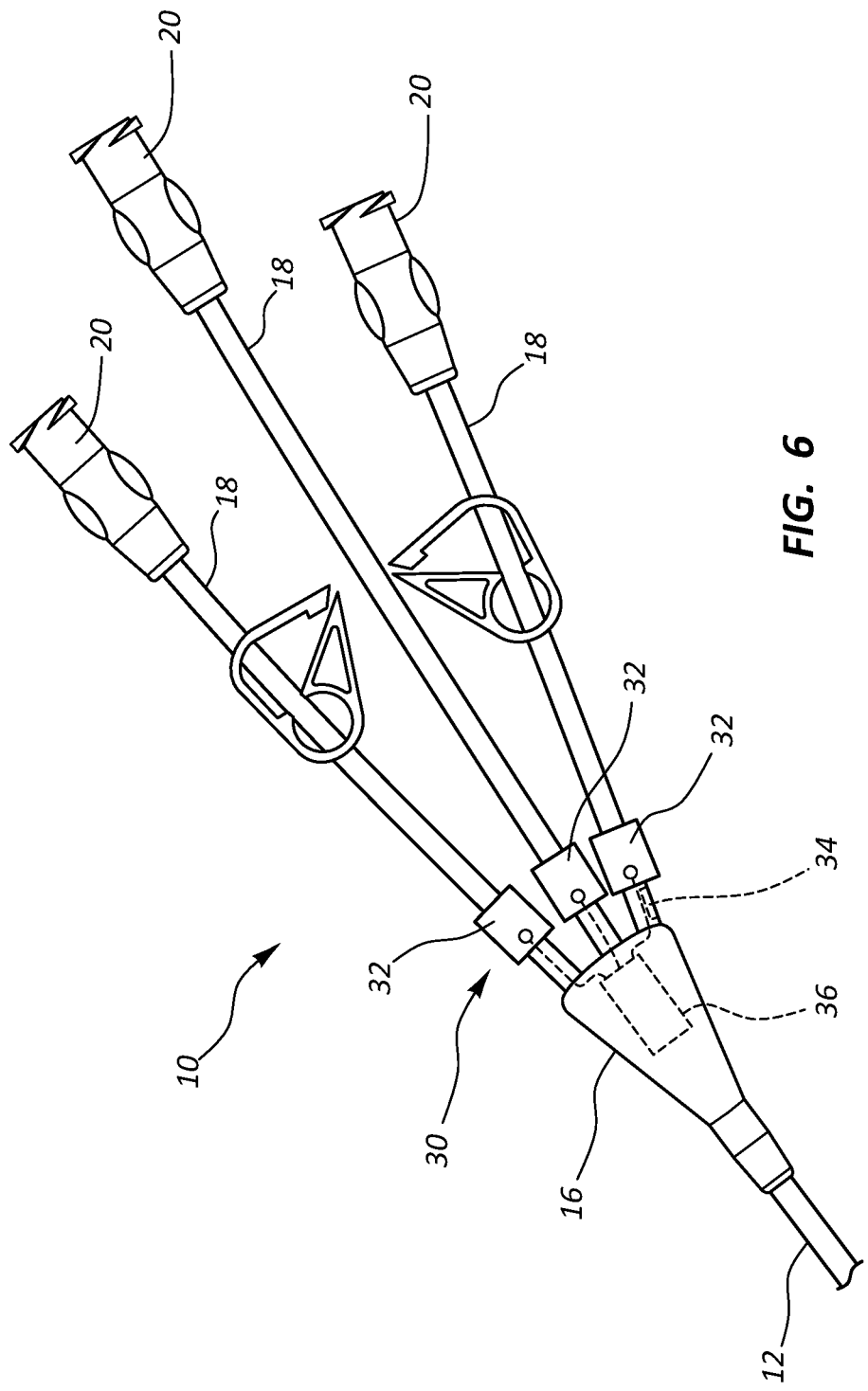
FIG. 6 is a perspective view of a catheter assembly in accordance with one embodiment.

FIG. 6 depicts the catheter 10 according to one embodiment, including three pressure sensors 30 in specified locations in the corresponding extension legs 18 and an ECG sensor 34 disposed in one extension leg, with each sensor operably connected to the PCB 36 disposed in the hub 16. FIG. 5 thus demonstrates that the number, type, and placement of the sensor(s) and PCB can vary from what has already been shown and described.

FIG. 7 depicts details of the sensor-equipped catheter 10 according to one embodiment, wherein the hub 16 includes an ultrasound assembly 80 comprising upper and lower PCBs 82A and 82B configured to control ultrasound transducers 84A and 84B, respectively. The ultrasound transducers 84A and 84B can be used to ultrasonically evaluate the fluid passageway, or lumen 92, of the bifurcation hub 16 to determine the contents of the lumen, as shown in FIGS. 8A-8D. For instance, FIG. 8A shows that when air is present in the lumen 92, no ultrasound signal is present, as depicted in an ultrasound signal graph 90 of FIG. 8A. In contrast, when a fluid, such as fluid A, is present in the lumen 92, the ultrasound transducers 84A and 84B return a signal of a specified voltage consistent with the composition of fluid A, as seen by the graph 90 of FIG. 8B. If a fluid B of differing composition from fluid A is present in the lumen 92, the ultrasound transducer 84A and 84B return a signal of specified voltage consistent with the composition of fluid B, as seen in the graph 90 of FIG. 8C. And when both fluid and air are present in the lumen 92, the graph 90 of FIG. 8D shows that a varying voltage signal is detected by the ultrasound transducers 84A and 84B. In this way, the ultrasound transducers 84A and 84B, coupled with the battery and PCB as discussed further above, can assist the user in determining the presence of particular substances in the lumen 92 of the hub 16, or the lumens of other catheter components, depending on placement of the ultrasound transducers. In another embodiment, only a single ultrasound transducer is employed.

Figure 9A:
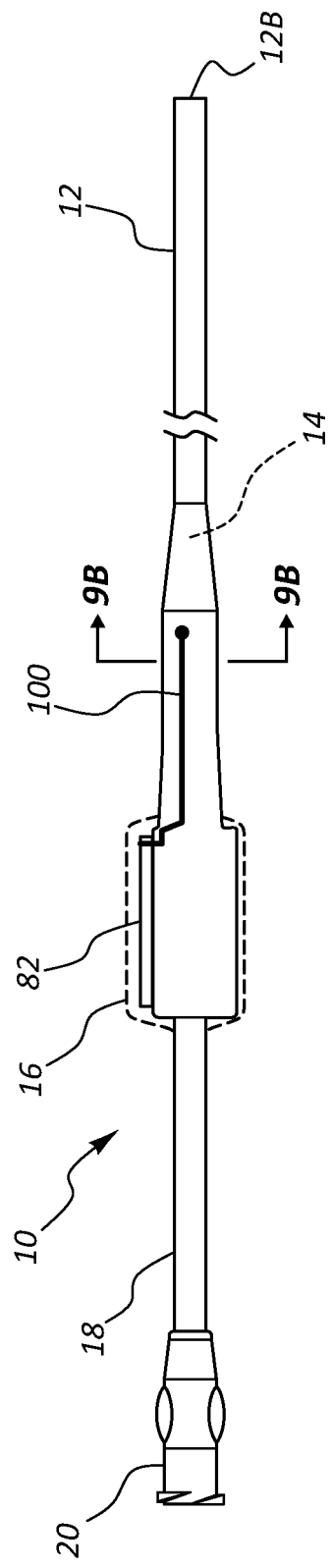
FIGS. 9A and 9B are various views of a catheter assembly in accordance with one embodiment.
Figure 9B:
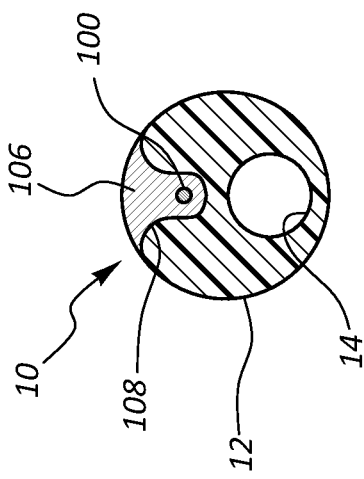

FIGS. 9A and 9B depict details of the sensor-equipped catheter 10 according to another embodiment, wherein the hub 16 includes a PCB 82 disposed therein and operably connected to a temperature sensor 100, such as a thermocouple in one embodiment, positioned so as to measure core body temperature via blood or other fluids present in the lumen 14 of the catheter. As FIG. 9B shows, the temperature sensor 100 can be placed in proximity to the lumen 14 via a skiving or cavity 108 longitudinally defined in the catheter tube 12 and/or hub 16. Potting 106 can be used to fill the cavity 108 about the temperature sensor 100. In one embodiment, the temperature sensor 100 includes a series 400 Model 401 thermistor available from Cole-Palmer Inc., Vernon Hills, Ill.

Figure 10:
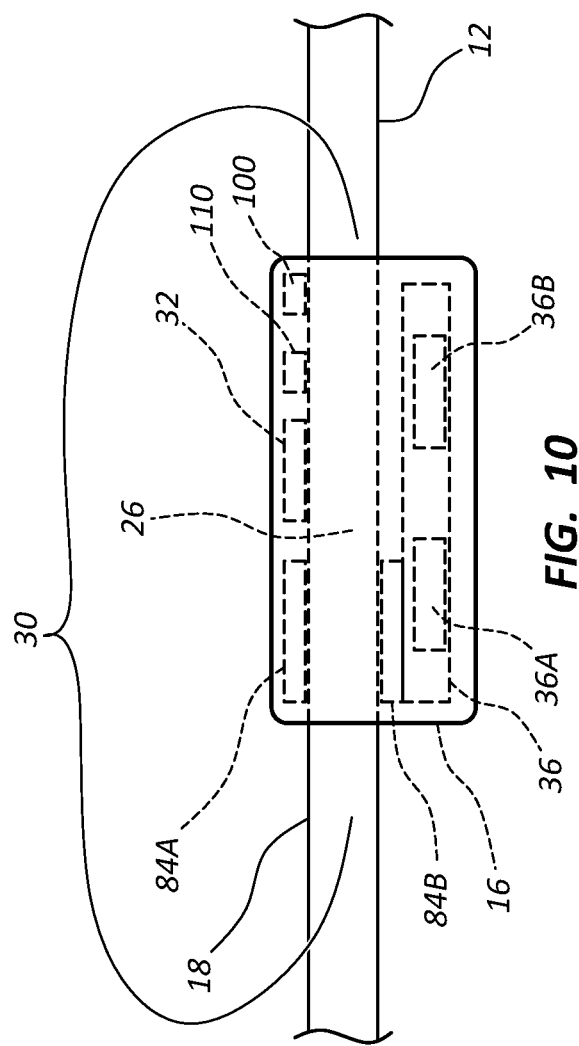
FIG. 10 is a partial cross-sectional view of a hub of a catheter assembly according to one embodiment.

FIG. 10 shows that, in one embodiment, a variety of sensors can be included as part of the sensor array 30 within the hub 16 or other suitable location. As depicted in FIG. 10, in one embodiment the hub 16 includes disposed therein the pressure sensor 32, the PCB 36 (including a processor 36A and a wireless communication module 36B), upper and lower ultrasound transducers 84A and 84B, a temperature sensor 100, and an oxygen sensor 110. The various sensors are arranged as needed in proximity to the fluid passageway 26 of the hub 16 so as to sense the relevant parameters as detected in the fluid present in the fluid passageway. The particular arrangement of the sensors can vary from what is shown here.

FIG. 11 shows that, in one embodiment a smartphone 100 can be the receipt location for wirelessly receiving data from one or more of the sensors of the sensor array, as discussed in the embodiments above. Examples of wireless modes by which the data can be transmitted include Bluetooth, Wi-Fi, radiofrequency, near-field communication (NFC), ANT, ZigBee, etc. Such data transmission can be relayed through a software-based application or other intermediary device. This enables a clinician to receive mobile updates and other sensor data 124 from the catheter 10 via a display 122 of the smartphone 120 (or by other mediums including sound, vibration, etc.) in order to be able to monitor the progress or condition of the patient. Other locations for receipt of the sensor data as described above include a patient electronic medical record ("EPR"), a patient monitoring apparatus, other mobile devices including electronic tablets and laptop computers, an electronic storage location, a computer server, a nurse station, medical equipment such as a pump attached to the catheter, and a variety of other destinations. It is appreciated that devices, components, computers, etc. that are located at the receipt location can perform operations on the received data, including analysis, trending, alarm functions, etc.

FIG. 12 depicts the catheter 10 according to another embodiment, wherein the catheter is shown inserted into an arm 128 of the patient such that a majority portion of the catheter tube 12 is disposed within the vasculature of the patient. The hub 16, including one or more sensors, is also shown operably connected to an auxiliary device, such as an armband 130, placed around the patient arm 128 via a connecting wire 134. The armband 130 is placed in proximity to the external portion of the catheter 10 in the present embodiment, though its location and particular shape, size, configuration, and body attachment scheme can vary in other embodiments. As shown, the armband 130 includes various components to work in concert with the sensor(s) of the catheter 10 via the connection wire 134, including the PCB 36 and a wireless communication module 136 (which in other embodiments is included with the PCB). Sensor data detected by the sensor(s) of the catheter 10 can be forwarded from the catheter 10 to the components of the armband 130 via the connecting wire 134, where the data can be processed (e.g., by the PCB 36) and/or transmitted to a remote location (e.g., by the wireless communication module 136). In another embodiment, the operable connection between the catheter 10 and the armband 130 is a wireless connection as well.

Placement of the PCB 36 and the wireless communication module 136 on the armband 130 frees up space on the catheter and may prevent the need for replacing relatively expensive components when the catheter 10 itself is periodically replaced with a new catheter. In such a case, the armband 130 can be simply connected to the new catheter, and the PCB 36 and wireless communication module 136 can begin to function with the new catheter as they did with the previous catheter. Note that various other components can also be included on the armband 130, including a battery for powering the sensor(s) included on the catheter, additional sensors including an ECG sensor, etc. As mentioned, the armband 130 is representative of other wearable and non-wearable auxiliary devices that can be operably connected to the sensor(s) of the catheter 10 in order to facilitate their operation. Also note that the components included on the armband/auxiliary device can be replaceable/reusable, in one embodiment. In one embodiment, the PCB, battery, and/or wireless communication module can be included on the catheter securement device. In another embodiment, the above-described components can be included on a platform that is removably attachable to the armband. In another embodiment, the armband or similar component includes a disposable shield to isolate it from the patient and/or to provide isolation from contaminants.

Figure 13:
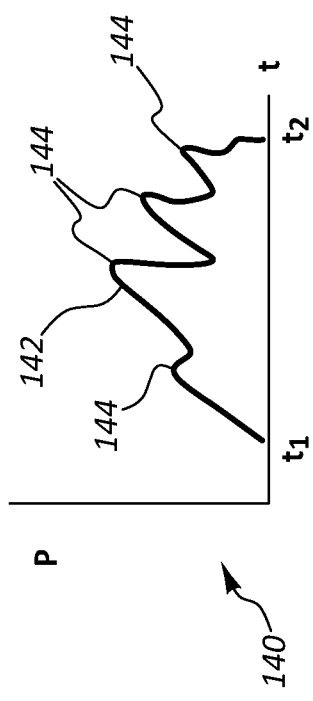
FIG. 13 is a pressure graph for a catheter assembly.

Several of the above-described embodiments include the pressure sensor 32 that is configured to sense data relating to the central venous pressure of the patient in which the catheter 10 is disposed. In another embodiment, data sensed by the pressure sensor 32 can be further employed to detect when an occlusion, such as a fibrin sheath or thrombus, may be present in the lumen 14 of the catheter tube 12. FIG. 13 shows a pressure graph 140 including a pressure curve 142 that depicts the level of pressure over time in the catheter tube lumen 14 as sensed by the pressure sensor 32, such as in the pressure sensor configuration of FIG. 10, for instance, during a flushing procedure wherein fluid is flushed through the catheter 10 by a user using a syringe connected to the luer connector 20 in order to maintain patency of the catheter tube lumen 14. As shown, the pressure curve 142 includes various pressure peaks 144 that are caused by the user pulsing the syringe with moments of additional pressure. This is performed so as to clear any minor obstructions that may have formed within the catheter tube lumen 14 or in other areas of the catheter fluid path. When an occlusion is present at the distal end 12B of the catheter tube and/or within the lumen 14 (see occlusion 178 in FIG. 15 for example), the pressure curve 142 will be elevated (i.e., shifted vertically upward along the pressure y-axis) or widened (i.e., lengthened along the time x-axis).

In more detail, hydraulic resistance R of a fluid is generally related to the fluid flow rate Q and infusion pressure P by the relationship:

$$P = Q * R, \quad (1)$$

which yields:

$$R = t1 \int t2\, P\, dt/V, \quad (2)$$

where V is a known volume of fluid to be infused into the catheter 10, t1 is the time at the beginning of a fluid infusion process, t2 is the time at the end of the fluid infusion process (referring to FIG. 13), noting that P indicates the instantaneous pressure during each moment of the fluid infusion procedure. Comparing the resistance R of the fluid infusion through the catheter tube 12 for a certain period of time (using the above equations) and comparing it with the resistance $R_0$ at a previous time, such as when the catheter 10 was first inserted into the patient and was considered un-occluded, or patent, can yield the percentage of possible occlusion in the catheter tube according to:

$$\% \text{ occlusion} = R/R_0 \quad (3)$$

Detection of an elevated pressure within the catheter fluid path by the pressure sensor 32, such as via the above-described calculations, can alert the user to a possible occlusion such that corrective measures can be taken. Further, data storage in a memory location located on the catheter 10 with the PCB 36 or remotely located in a patient electronic medical record (or other remote storage location) can be employed to measure the catheter flushing pressure over time so as to detect pressure changes over time. This data comparison over time can be performed for any one of the sensors located on the catheter 10, as may be appreciated. Of course, the data sensed by the sensors and stored in a memory location can be used for a variety of other uses as well, including historical trends, etc.

Figure 14:
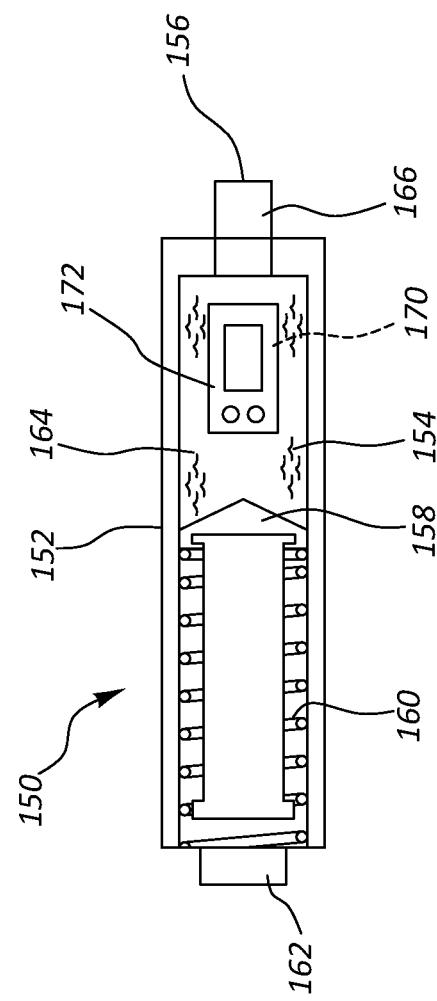
FIG. 14 is a partial cross-sectional view of a pressure-sensing syringe in accordance with one embodiment.

FIG. 14 depicts various details of a pressure-sensing syringe 150 according to one embodiment, including a housing 152 that defines a cavity 154 with a distal end fluid outlet 156. A plunger 158 is disposed within the cavity 154 and is attached to a spring 160, initially disposed in a compressed state and releasable by a release button 162 disposed on a proximal end of the syringe 150. A known quantity of 0.9% normal saline 164 or other suitable liquid is disposed in the cavity distal to the plunger 158 such that the saline exits the fluid outlet 156 when the spring 160 is actuated by the release button 162. The saline 164 ejected by the syringe 150 is injected into the extension leg 18—then through the hub 16 and lumen 14 of the catheter tube—when the syringe is operably attached to the corresponding luer connector 20.

A pressure sensor 166 is included at the fluid outlet 166 to measure the pressure of the known quantity of saline 164 as it exits the fluid outlet 156 and enters the catheter 10 to which the syringe 150 is connected. A processor unit 170 and a display/control unit 172 are included to measure and calculate (such as via the equations described further above) the pressure present as the saline 164 is ejected by the plunger 158 through the fluid outlet. Further calculations can be performed by the processor unit 170 to determine the hydraulic resistance of the injection, thus yielding the amount of occlusion present in the fluid path of the catheter 10, using the known volume of injected saline 164, the injection pressure as measured by the pressure sensor 166, and the amount of time needed for injection of all the saline to occur. In one embodiment, the user can input the size of the catheter tube lumen 14 and the length thereof via the display/control unit 172.

The results describing the amount of any occlusion present in the catheter fluid path (such as in % of fluid path occluded, for instance) can be depicted on the display/control unit 172 or wirelessly transmitted to a receipt location via a wireless communication module included with the processor unit 170, for instance. Corrective measured can then be taken by the user, if needed.

Note that historical pressure/occlusion data can be stored by a memory location of the processor unit 170, for instance, for call-up and depiction by the display/control unit 172, in one embodiment. In one embodiment, the plunger 158 of the syringe 150 is manually depressible by the user, thus obviating the need for the spring 160, or can be a pressurized gas source to push the plunger, etc. The location of the pressure sensor 166 can also vary from what is shown and described herein.

Note that, in another embodiment, the pressure sensor 32 can be used to determine when the catheter tub 12 has been malpositioned within the vasculature by sensing pressure differences between expected values for a proper placement and actual sensed values as detected by the pressure sensor. When this situation occurs, proper steps to correct the malposition can be taken. In another embodiment, the pressure sensor 32 and the electrical (ECG) sensor 34 can work in concert to detect catheter malposition based on venous pressure readings and ECG signal analysis.

Figure 15:
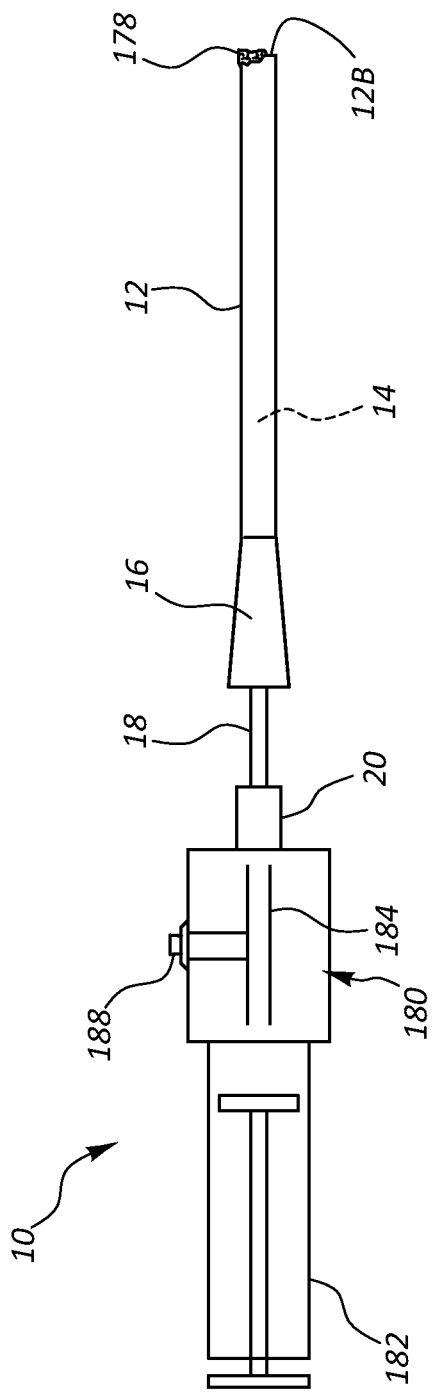
FIG. 15 is a partial cross-sectional view of a pressure-indicating catheter assembly according to one embodiment.

FIG. 15 depicts various details of the catheter 10 that includes the ability to detect occlusions, such as a partial occlusion 178 shown at the distal end 12B of the catheter tube 12, according to one embodiment. As shown, the catheter 10 includes a pressure detection module 180 operably attached to the luer connector 20 of the catheter 10. A syringe 182 is attached to a proximal end of the pressure detection module 180 so as to provide an injection of saline or other suitable fluid through a flow lumen 184 of the pressure detection module 182 and into the extension leg 18 to flow through the catheter 10.

As shown, the pressure detection module 180 includes a pressure indicator 188 in fluid communication with the flow lumen 184. The pressure indicator 188 is configured to extend an indicator piece outward when a predetermined pressure is encountered in the flow lumen 184 of the pressure detection module. As such, when a fluid pressure in excess of the predetermined pressure is encountered in the catheter lumen 14 during fluid injection into the system by the syringe 182 (or other suitable fluid injection device), the pressure buildup extends proximally through the hub 16, extension leg 18, and flow lumen 184, causing the indicator piece of the pressure indicator to extend outward, thus indicating to the user that an occlusion may be present. It is appreciated that indicator pieces of differing configurations can be employed. In the present embodiment, the pressure detection module 180 is a separate component attachable to the catheter 10; in other embodiments the pressure detection module is integrally formed with the catheter.

Figure 16:
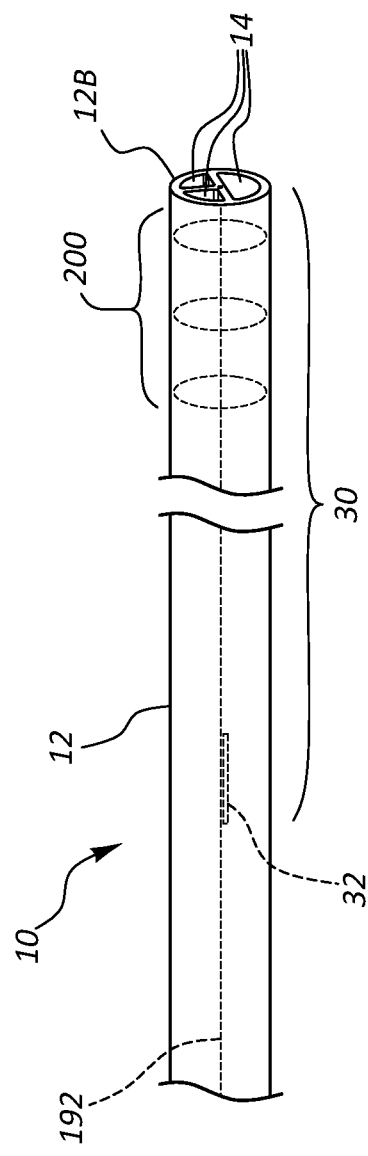
FIG. 16 is a view of a distal portion of a catheter assembly according to one embodiment.

FIG. 16 depicts possible locations for sensors of the sensor array 30 in the catheter tube 12. As shown, various sensors 200 of the sensor array 30 are disposed proximate the distal end 12B of the catheter tube 12, together with the pressure sensor 32 disposed proximally to the other sensors. FIG. 16 further shows that a connection wire 192 extends along a central portion of the catheter tube, e.g., within a septum separating the lumens 14 from one another, to power the sensors 200 of the sensor array 30. In another embodiment, the connection wire 192 can be disposed in a dedicated lumen extending the length of the catheter tube. Note that placement of the sensor(s) a distance proximal to the catheter tube distal end 12B, such as the pressure sensor 32 here, enables the catheter tube 12 to be distally trimmable.

Figure 17:
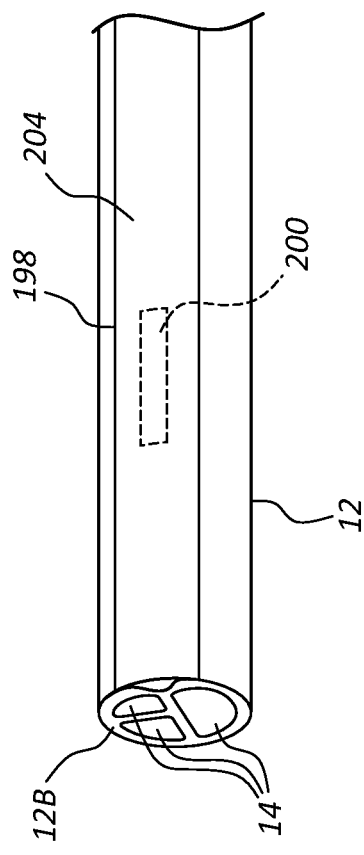
FIG. 17 is a view of a distal portion of a catheter assembly according to one embodiment.

FIG. 17 depicts another configuration for including a sensor 200 in the catheter tube 12, wherein the sensor 200 is disposed in the wall of the catheter tube 12 within a skive cut 198 longitudinally defined in the wall. Potting 204, such as a thermally conductive epoxy, polyurethane, or RTV potting, is included to cover the sensor 200. In one embodiment, the sensor 200 includes a glucose sensor for sensing blood glucose levels and is not potted such that the glucose sensor has direct contact with the blood. These and other possible sensor locations are therefore contemplated.

Figure 18:
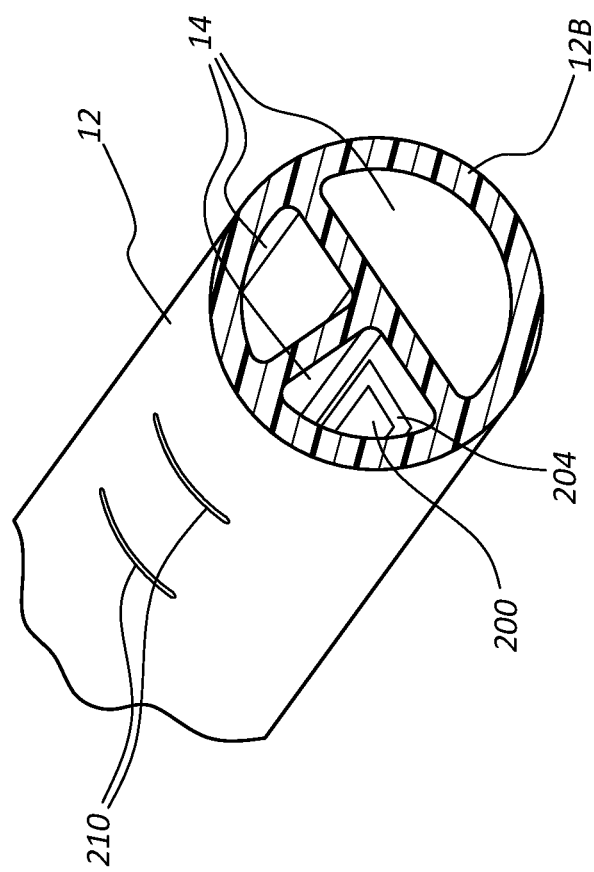
FIG. 18 is a perspective view of a distal portion of a catheter assembly according to one embodiment.

FIG. 18 depicts another configuration for including a sensor in the catheter tube 12, wherein the sensor 200 is disposed on an inner surface of one of the lumens 14 of the catheter tube 12 proximate the distal end 12B thereof. Potting 204 can be included to insulate and cover the sensor 200 as needed. In one embodiment, the potting 200 protects the sensor 200 from exposure to liquids while enabling heat to be transmitted therethrough. FIG. 18 further shows that wire-based electrodes 210 can be disposed in the wall of the catheter tube 12 proximate the distal end 12B of the catheter tube 12 so as to be exposed on an outer surface thereof. The sensors 210 can be formed as concentrically disposed sensors that can be employed to make volumetric measurements to determine the size of the vessel in which the catheter tube is disposed, thus assisting the user in determining a possible malposition of the catheter tube in an undesired vessel. These and other possible sensor configurations are therefore contemplated.

FIG. 19 depicts various details of a flush sensor 222 for detecting when the desired periodic flushing of the catheter 10 with a fluid has occurred, also referred to herein as a flush state of the catheter tube 12. As shown, the flush sensor 222 is disposed within a cavity 220 of the luer connector of the catheter extension leg 18, though other locations can be employed for the sensor. The flush sensor 222, also referred to herein as a detection module, includes a lever 224 biased to an extended position by a spring 226, as shown. The flush sensor 222 is operably connected to a processor of a PCB (such as the PCB 36 shown in FIG. 10) or other suitable component (disposed within the luer connector 20, for instance) to govern its operation and process its sensed data.

In operation, when a syringe or other component is inserted into the cavity 220 of the luer connector 20 to flush the catheter 10 with saline or other suitable fluid, the lever 224 of the flush sensor 222 is depressed, which causes a signal to be sent to the processor indicating that a flushing procedure is occurring. The time of flushing or other data relating to the flushing procedure can be noted, stored or used by the processor, or wirelessly transmitted to a receipt location in a manner similar to that discussed further above. In one embodiment, the flush sensor 222 and the processor of the PCB 36 are referred to as a flush sensor assembly, though it is appreciated that the assembly can include additional components. In another embodiment, an electrical sensor can be employed as the flush sensor, wherein the electrical sensor includes a circuit that is broken each time a component is inserted into the connector 20. Breaking of the circuit can reset a timer circuit to measure the next period until the flush sensor is again activated.

In one embodiment, for instance, it is desired that the catheter 10 be flushed at least once every 12 hours. When the flush sensor 222 detects a flushing procedure as described above, a timer circuit in the processor is re-set to begin counting time to measure the next time period until the flush sensor 222 is again depressed to indicate a new flushing procedure.

FIG. 20 shows that a light array 230, such as a collection of a red LED light, yellow LED light, and green LED light, can be included on a surface of the luer connector 20 to visually indicate the flushing status of the catheter 10, in one embodiment: a green light indicates less than 10 hours have elapsed since the last flushing procedure was detected; a yellow light indicates more than 10 hours but less than 12 hours have elapsed since the last flushing procedure; a red light indicates that more than 12 hours have elapsed since the last flushing procedure. The processor governs the operation of the light array and it is understood that the lights can vary in number size, location, purpose, indicated elapsed time, etc. Further, it is appreciated that other types of sensors, including sensors that detect the presence of liquid within the luer connector cavity 220, can also be employed to detect flushing procedures.

In another embodiment, the light array 230 can be used as follows: the green light flashes after an acceptable flushing procedure has been performed; the red light blinks after a non-acceptable or incomplete flushing procedure has occurred; the yellow light blinks or is turned on to indicate a possible occlusion present in the catheter tube 12. In yet another embodiment, the yellow light (or other light) can be lit to serve as a reminder to flush the catheter 10.

It is appreciated that in another embodiment the luer connector 20 or other portion of the catheter 10 can include a push button (or other user-activated component) that can be depressed at the time of catheter flushing, thus re-setting the timer circuit. In this case, a counting circuit can also be included to count the number of times the connector 20 or other component is accessed.

FIG. 21 shows that the light array 230 can be disposed in other locations on the catheter 10, including in this embodiment disposal on the hub 16. These and other possible locations, such as the catheter tube or extension legs, or the armband 130 of FIG. 12 for example, are therefore contemplated. In other embodiments, the light array can be employed to alert the user to other sensed conditions, including elevated body temperature/fever, onset of sepsis (see further below), catheter occlusion, low blood oxygen levels, etc. Further, other indicia can be employed, in addition to lights, to alert the user with respect to the sensor data, including sound, vibration, etc. either on the catheter itself or at the remote receipt location to where the data is wirelessly transmitted.

Note that the flush sensor 222 can be included in other areas as well, including a needleless connector that is configured to operably attach to the luer connector, for instance.

In one embodiment, the pressure sensor 32 can be used—alone or in concert with the flush sensor 222 described above—to detect and/or characterize flushing procedures. For instance, in one embodiment the flush sensor 222 can be used to detect a flushing procedure, while the pressure sensor 32 can sense the amount of pressure present during the flushing procedure, thus detecting possible occlusions. Indeed, in one embodiment, the pressure sensor 32 can be used to determine flushing frequency of the catheter 10, flushing technique, flushing time, number of times of catheter access, time expired since last catheter access, etc., by measuring pressure within the lumen 14 of the catheter as a function of time, using timer circuitry included on the PCB 36, for instance. Such sensor data can be stored by a memory location located on the PCB 36, for instance, or transmitted to another local or remote receipt location, as has been described. Processing to determine such monitoring can be performed by a processor included on the PCB 36 or remotely.

In one embodiment, sensor data from catheter sensors, such as the pressure sensor 32 and a core body temperature sensor, can be employed to detect patient conditions, such as sepsis. In particular, respiratory rate, heart rate, and body temperature can be sensed via the pressure sensor 32 and the core body temperature sensor 100 included with the catheter 10, such as in the configuration shown in FIG. 10. These three parameters comprise three of four parameters that are typically employed to determine the onset of sepsis. As such, monitoring of these parameters via the catheter 10 as described herein can be used to prevent detect and ameliorate complications from sepsis, in one embodiment.

Figure 22:
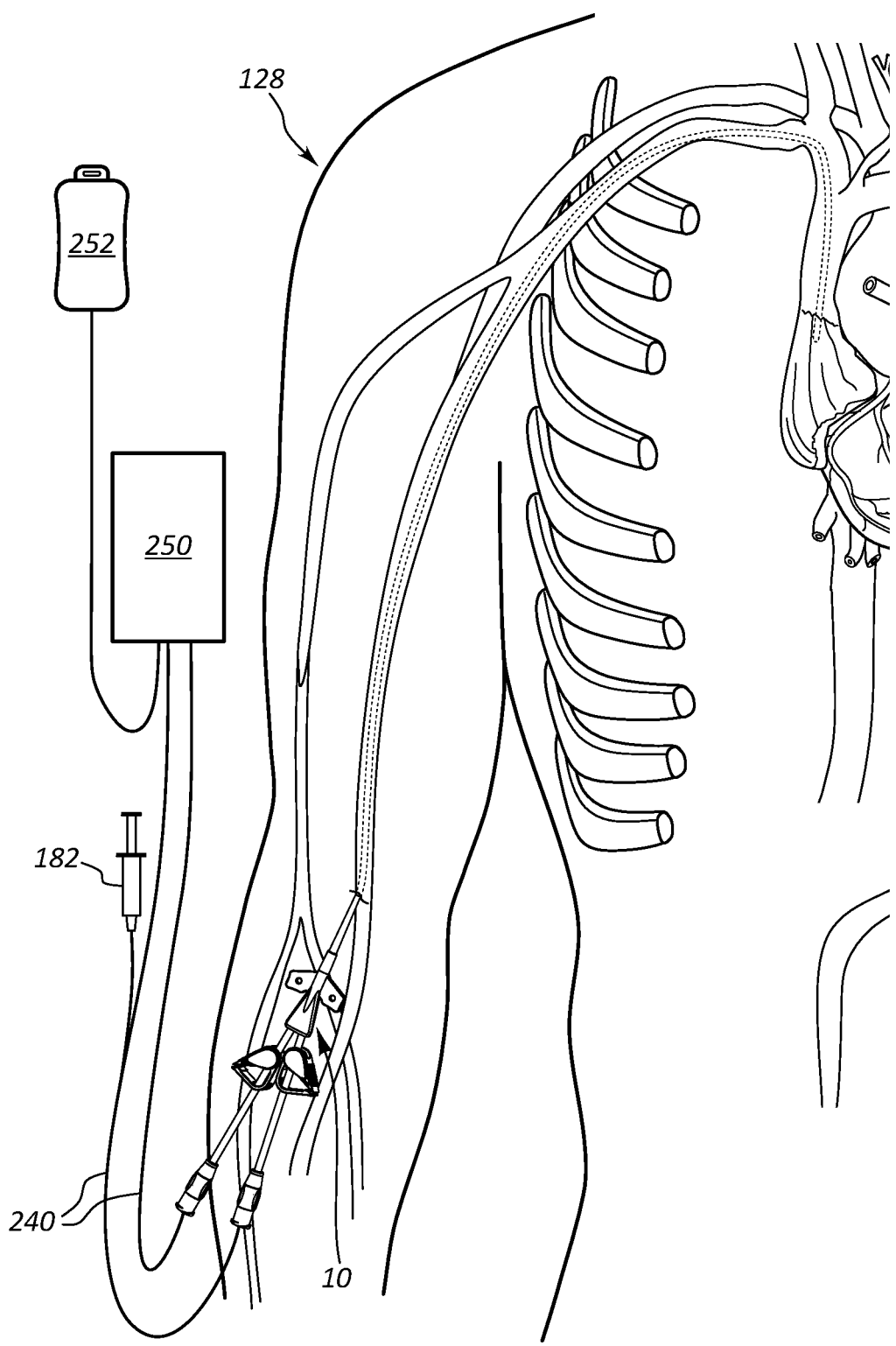
FIG. 22 is a simplified view of a pump system for use with a catheter according to one embodiment.

FIG. 22 depicts a sensor-based catheter assembly according to another embodiment. In detail, the catheter 10 is shown with its catheter tube 12 disposed within the vasculature of the patient and the two luer connectors 20 operably connected to supply lines 240 configured to both provide fluid to and remove fluid from the lumens of the catheter. A pump unit 250 is included to enable fluid movement through the supply lines 240. A saline fluid drip assembly 252 is also included to provide fluid to the pump unit for movement through the supply lines, if needed or desired. A syringe, such as the syringe 182, is included to provide an additional fluid inlet in a corresponding one of the supply lines 240.

Figure 23:
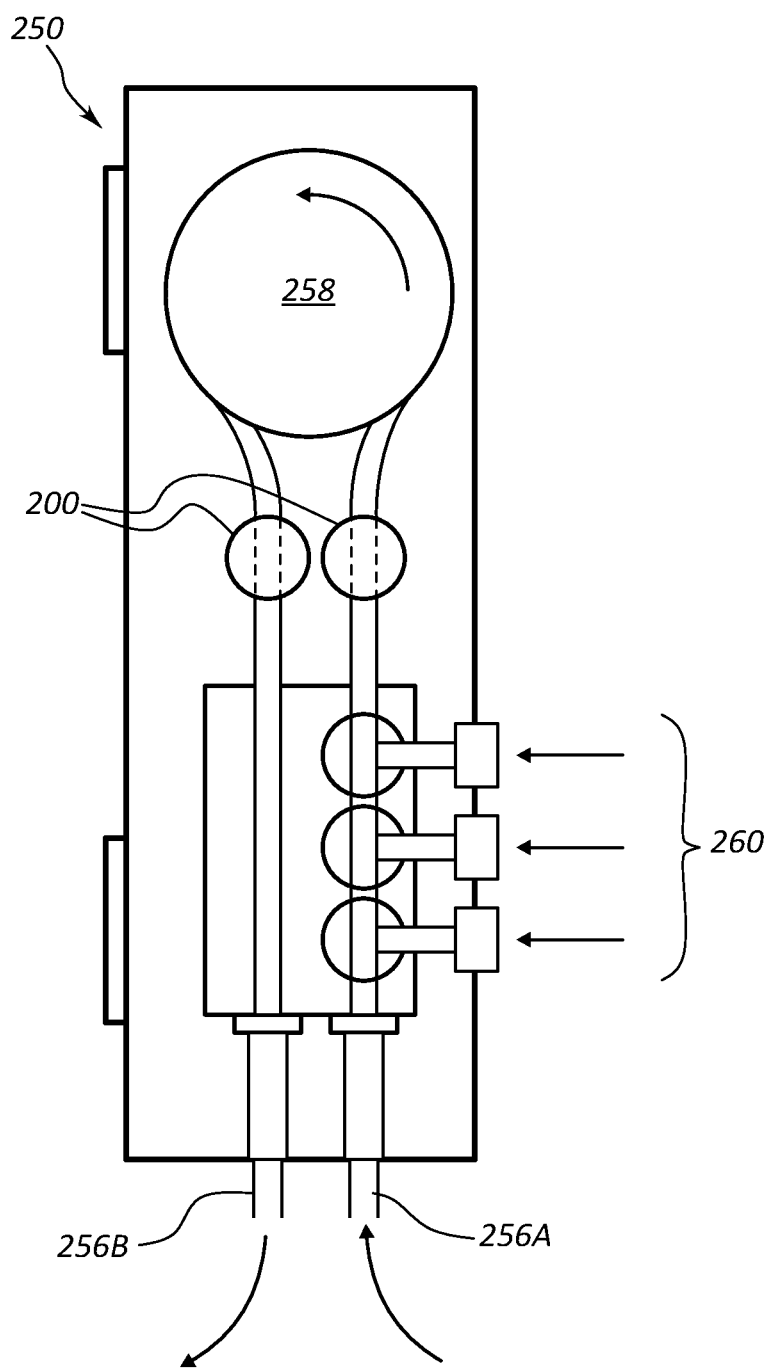
FIG. 23 is a side view of a pump unit of the pump system shown in FIG. 22.

FIG. 23 depicts further details of the pump unit 250 of FIG. 22, including a fluid inlet 256A and a fluid outlet 256B that are configured to operably connect with the corresponding supply lines 240 (FIG. 22) to bring blood or other fluid from within the patient vasculature via the catheter 10 (through the fluid inlet 256A) to the pump unit 250 and to return the fluid to the patient vasculature (through the fluid outlet 256B) via the catheter. A pump 258 is included in the pump unit 250 to cause the movement of the fluid. Additionally, various input ports 260 are included on the pump unit 250 in fluid communication with the fluid inlet 256A to enable additional fluids to be input, including heparin, saline, arterial input, etc.

One or more sensors 200 are also included in the pump unit 250 and arranged so as to measure one or more physiological aspects of the patient blood. Examples of such sensors include a glucose meter, oxygen sensor, lactic acid sensor, cardiac output sensor, etc. The location of the sensors 200 can vary from what is shown here. Disposal of the sensors 200 in the pump unit 250 as opposed to the on the catheter 10 itself enables sensors of relatively greater size to be employed without unduly increasing the size of the catheter.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A catheter assembly for insertion into a body of a patient, comprising:
   an elongate catheter defining at least one lumen extending between a proximal end and a distal end;
   a flush sensor integrated in the proximal end of the catheter outside of the body of the patient when the distal end of the catheter is inside the body of the patient, the flush sensor configured to detect a flush state of the catheter;
   a pressure sensor coupled to a distal portion of the catheter; and
   an auxiliary device separated from the catheter, the auxiliary device operably attached to the flush sensor and the pressure sensor, the auxiliary device including a printed circuit board and a battery.

2. The catheter assembly according to claim 1, wherein the auxiliary device is configured to be worn on the body or clothing of the patient.

3. The catheter assembly according to claim 1, wherein the auxiliary device includes at least one removable or reusable component.

4. The catheter assembly according to claim 1, wherein the auxiliary device is operably connected to the flush sensor and the pressure sensor of the catheter assembly via a connecting wire.

5. The catheter assembly according to claim 1, wherein the auxiliary device includes a wireless communication module.

6. The catheter assembly according to claim 1, wherein the auxiliary device includes an armband.

7. The catheter assembly according to claim 1, further comprising an oxygen sensor, a temperature sensor, an ultrasound transducer, an electrical sensor configured to detect ECG signals, and a glucose sensor.

8. The catheter assembly according to claim 1, further comprising a communication module configured to wirelessly transmit data sensed by the flush sensor and the pressure sensor to a receipt location, wherein the auxiliary device is a securement device configured to removably secure the catheter assembly to the patient, and wherein the communication module is included in the securement device.

9. The catheter assembly according to claim 8, wherein the communication module is included on the printed circuit board, the printed circuit board included with the securement device.

10. The catheter assembly according to claim 8, wherein the receipt location is selected from the group consisting of a smartphone, a storage device, a patient electronic medical record, a mobile device, a computer server, a laptop computer, a nurse station, and a printer.

11. The catheter assembly according to claim 8, wherein the communication module is configured to transmit the data sensed by the flush sensor and the pressure sensor via at least one of Bluetooth, Wi-Fi, near-field communication, and radiofrequency signals.

12. The catheter assembly according to claim 1, wherein the flush sensor is configured to be activated when a component is operably connected to the catheter assembly.

13. The catheter assembly according to claim 12, wherein the flush sensor includes a lever that is configured to be displaced when the component is operably connected to the catheter assembly.

14. The catheter assembly according to claim 13, wherein the flush sensor is included in at least one of a luer connector and a needleless connector on the proximal end of the catheter.

15. The catheter assembly according to claim 14, wherein the pressure sensor is configured to operate with the flush sensor to detect when the catheter assembly is being flushed with fluid.

16. The catheter assembly according to claim 15, wherein detection of an elevated pressure by the pressure sensor permits a user to determine a relative patency of the catheter.

17. The catheter assembly according to claim 1, further comprising at least one light disposed on the catheter assembly, the light configured to operate in conjunction with the flush sensor and the pressure sensor to alert a user.

18. The catheter assembly according to claim 1, further comprising a temperature sensor, the pressure sensor and the temperature sensor configured to sense a respiratory rate, a heart rate, and a body temperature of the patient in order to determine whether a sepsis condition is present.

19. The catheter assembly according to claim 1, further comprising a LED light array.

20. The catheter assembly according to claim 19, wherein the LED light array includes different colored lights to indicate time elapsed from a flushing procedure.

21. The catheter assembly according to claim 20, wherein the LED light array includes flashing lights to indicate a status of the flushing procedure or an occlusion of the at least one lumen of the catheter.

* * * * *